(12) United States Patent
Singh

(10) Patent No.: US 7,854,932 B2
(45) Date of Patent: Dec. 21, 2010

(54) IMMUNOGENIC COMPOSITIONS COMPRISING PROGASTRIN AND USES THEREOF

(75) Inventor: Pomila Singh, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/002,979

(22) Filed: Dec. 19, 2007

(65) Prior Publication Data

US 2008/0187577 A1 Aug. 7, 2008

Related U.S. Application Data

(60) Provisional application No. 60/875,732, filed on Dec. 19, 2006.

(51) Int. Cl.
*A61K 39/395* (2006.01)
*C12Q 1/00* (2006.01)

(52) U.S. Cl. .............. 424/178.1; 424/130.1; 435/325; 435/7.23

(58) Field of Classification Search .............. None
See application file for complete search history.

(56) References Cited

U.S. PATENT DOCUMENTS

2003/0064949 A1* 4/2003 Nielsen et al. ............... 514/44
2004/0109864 A1* 6/2004 Sharma et al. ............ 424/155.1

OTHER PUBLICATIONS

Singh et al, Oncogene, vol. 26, p. 425-440, Jan. 2007.*
Molina et al, Tumor boil, 25:56-61, 2004.*
Sharma et al, Exp and Mol Path, 81:136-145, pub online, Apr. 2006.*
Singh, P. et al. Gastrin Gene Expression is Required for the Proliferation and Tumorigenicity of Human Colon Cancer Cells.: *Cancer Res.*, Sep. 15, 1996, vol. 56, No. 18, pp. 4111-4115.
Siddheshwar, RK et al. Plasma Levels of Progastrin but not Amidated Gastrin or Glycine Extended Gastrin are Elevated in Patients with Clolrectal Carcinoma: *Gut*, 2001, vol. 48, No. 1, pp. 47-52.
Madoiwa, S. et al. Annexin 2 and Hemorrhagic Disorder in Vascular Intimal Carcinomatosis: *Thrombosis Research*, 2007, vol. 119, No. 2, pp. 229-240.

* cited by examiner

*Primary Examiner*—Larry R. Helms
*Assistant Examiner*—Lei Yao
(74) *Attorney, Agent, or Firm*—Benjamin Aaron Adler

(57) ABSTRACT

The present invention is drawn to immunotherapeutic methods to treat tumors/cancers that produce progastrin ectopically or are dependent on progastrin for their growth. Disclosed herein are immunogenic compositions comprising agents that target progastrin, agents that target the progastrin receptor, annexin II, or both. Such a composition may be administered in combination with chemotherapy or to an individual who had been previously subjected to chemotherapy or radiation therapy. The cancers that may be treated using such a composition may include but are not limited to colon cancer, breast cancer, lung cancer or pancreatic cancer.

9 Claims, 22 Drawing Sheets

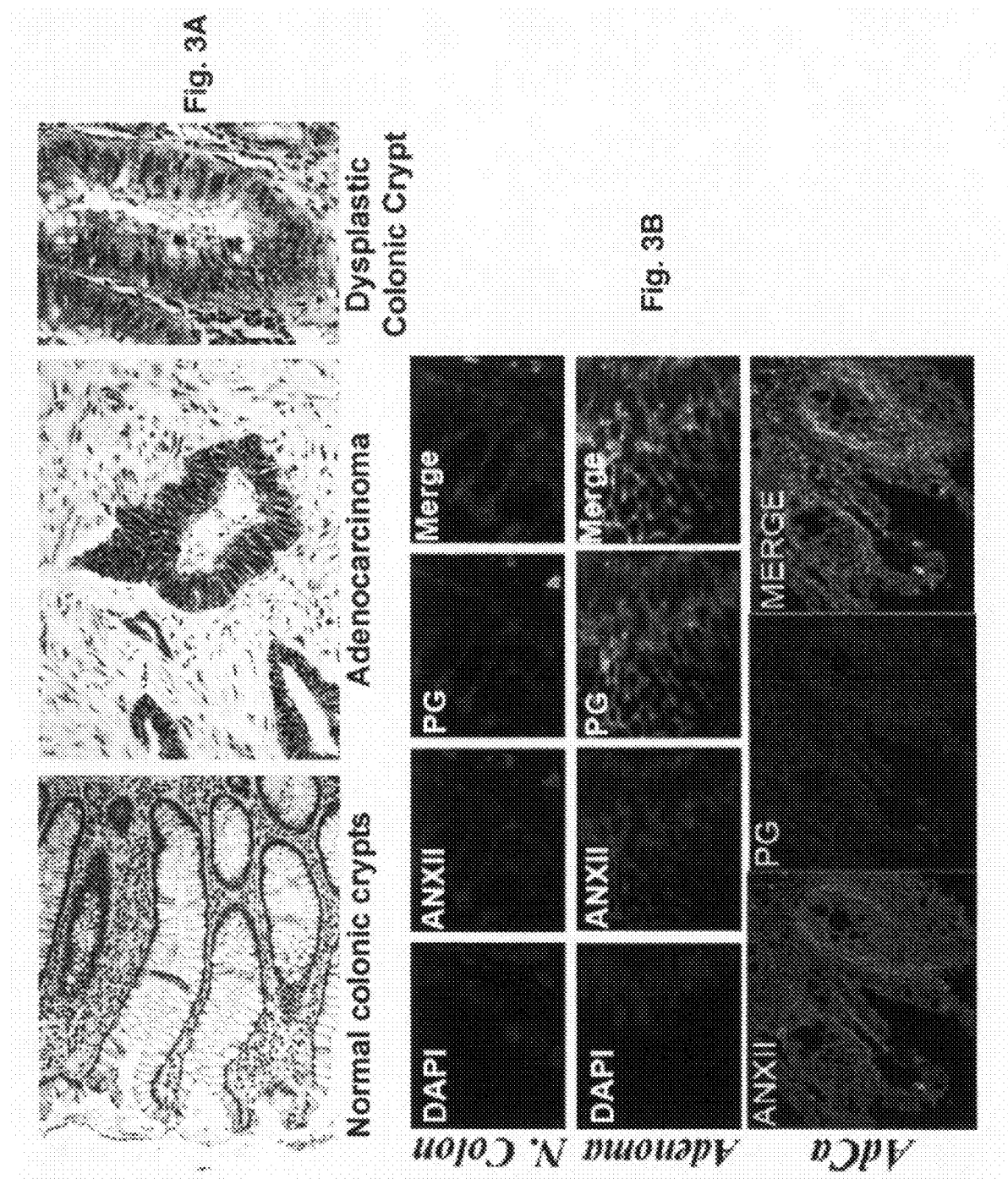

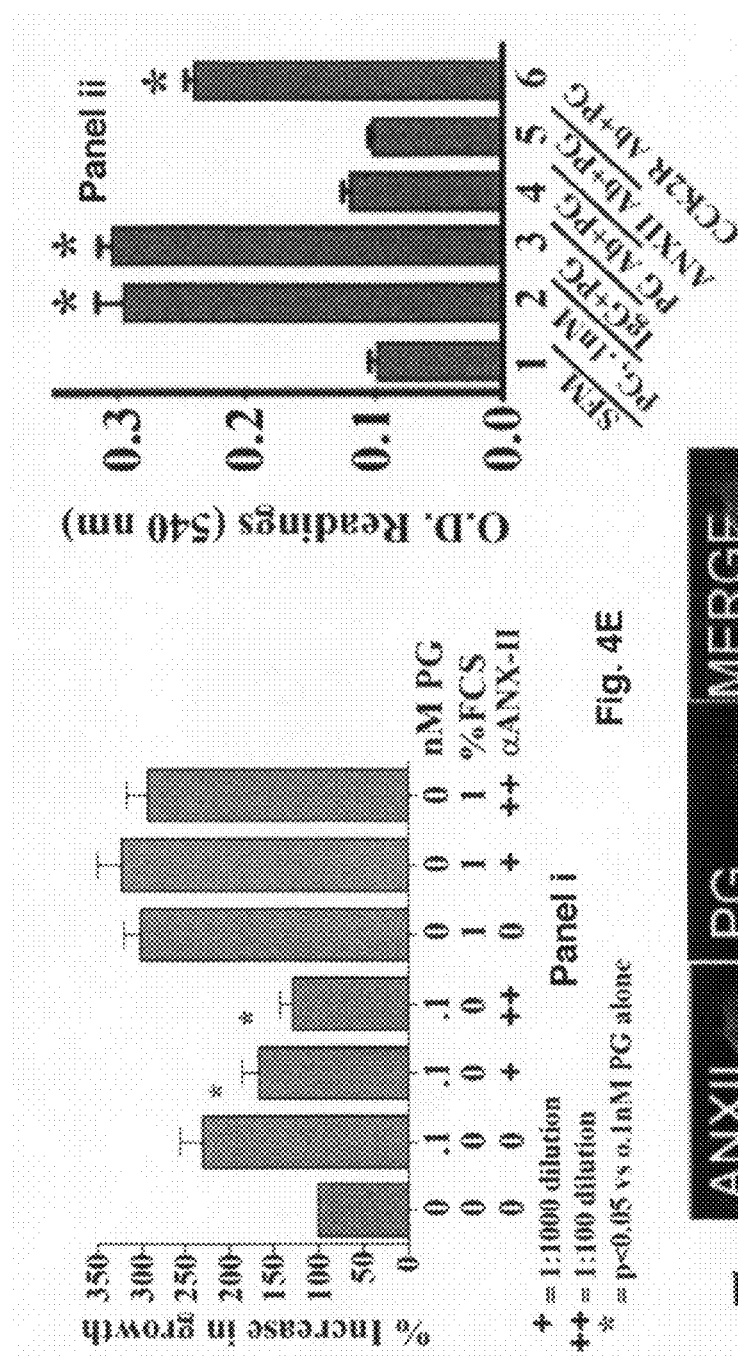
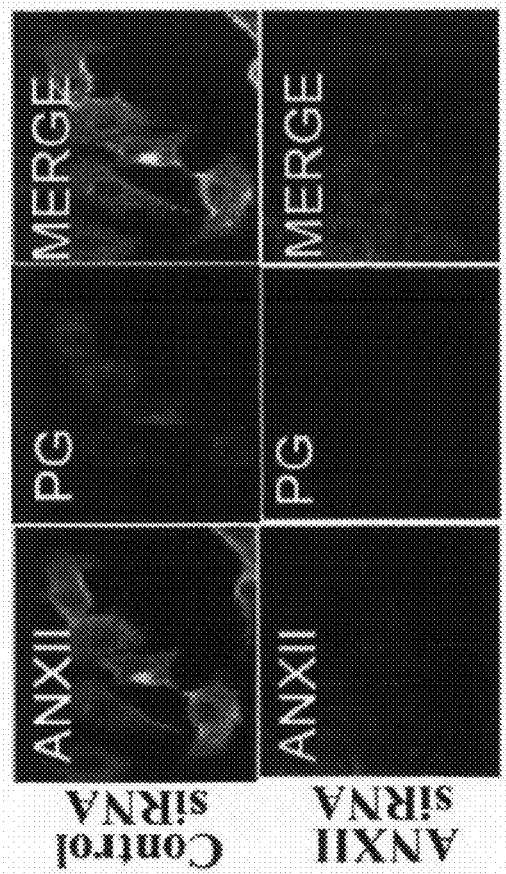
Fig. 4E
Fig. 4F

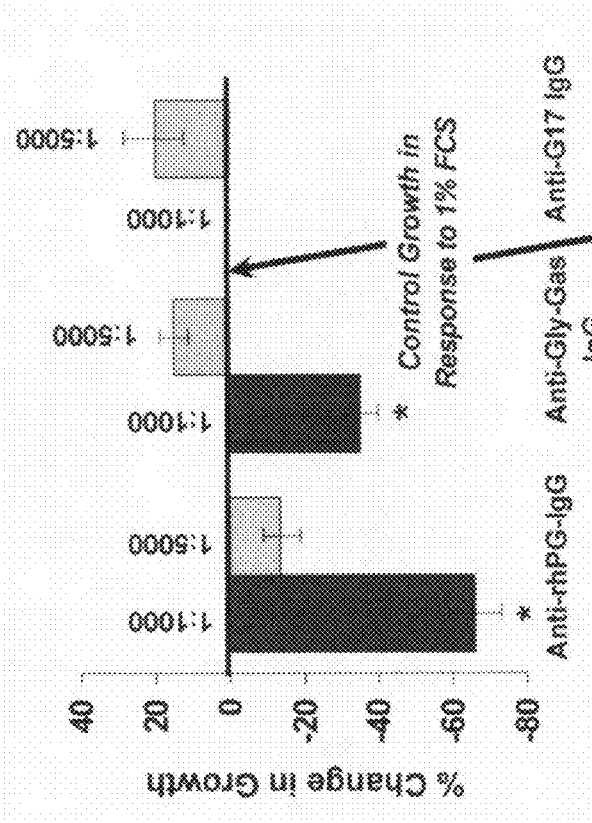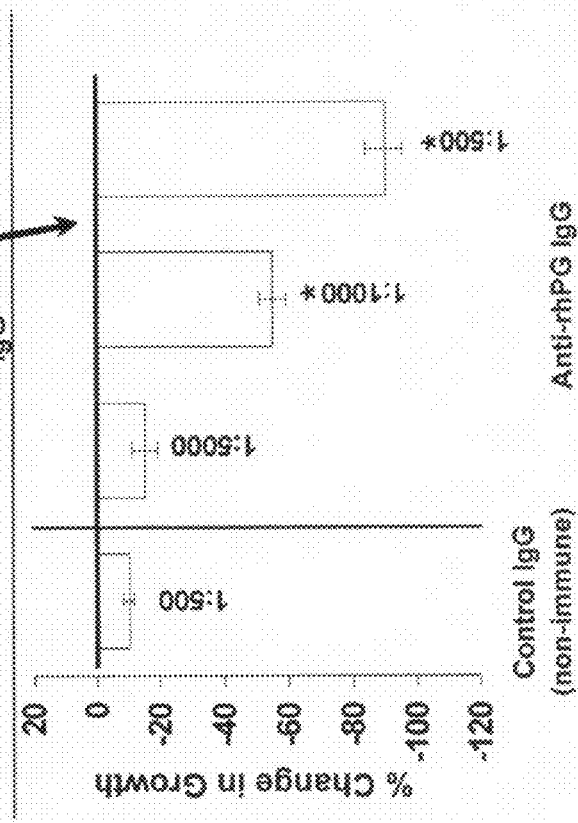
Fig. 5A
Fig. 5B

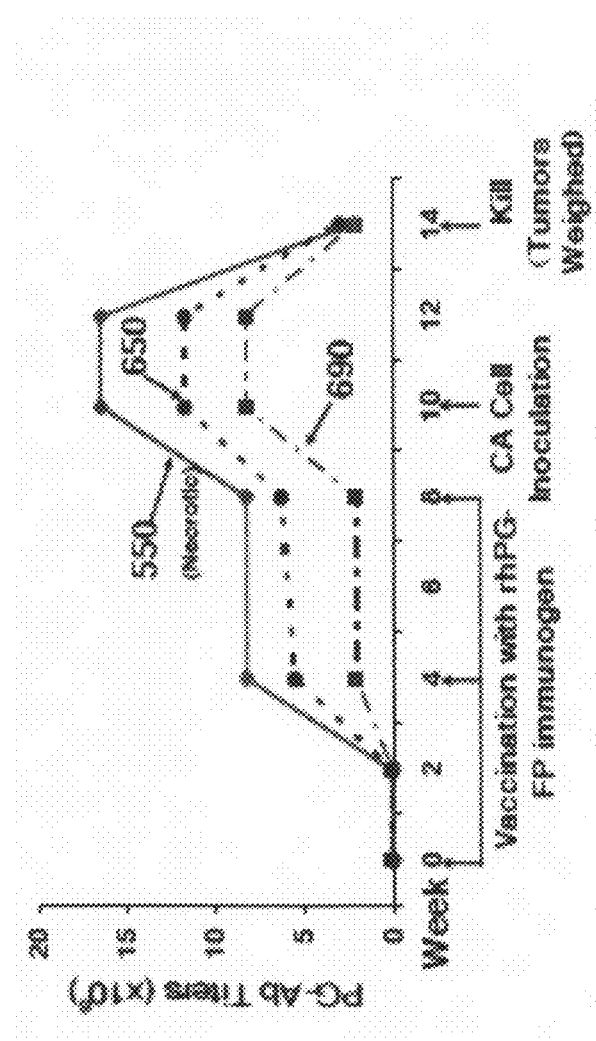
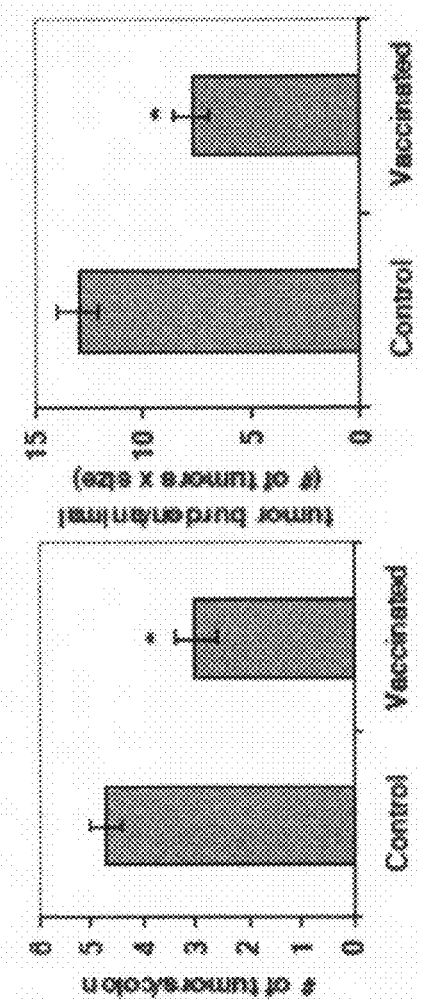
Fig. 6A
Fig. 6B
Fig. 6C

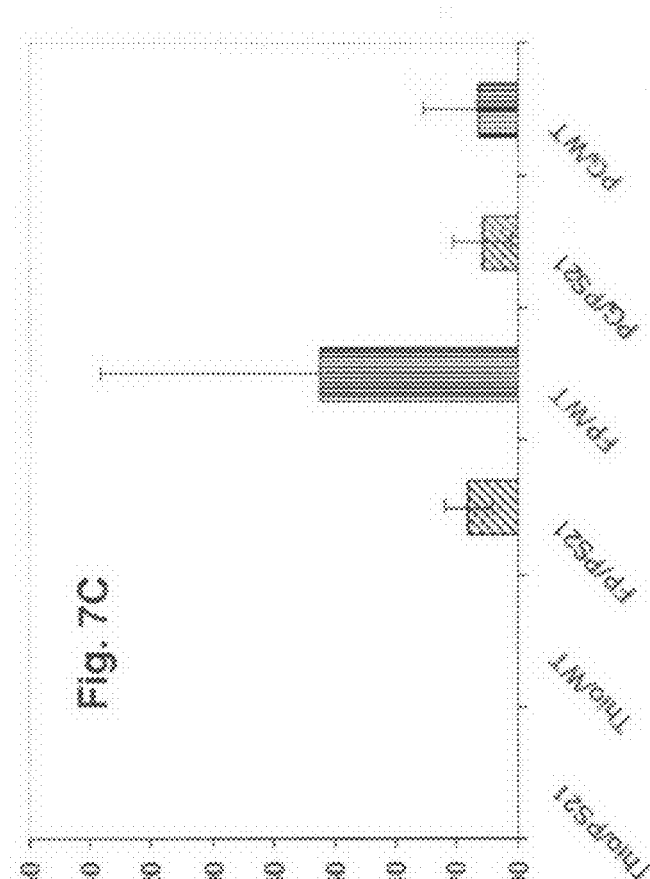
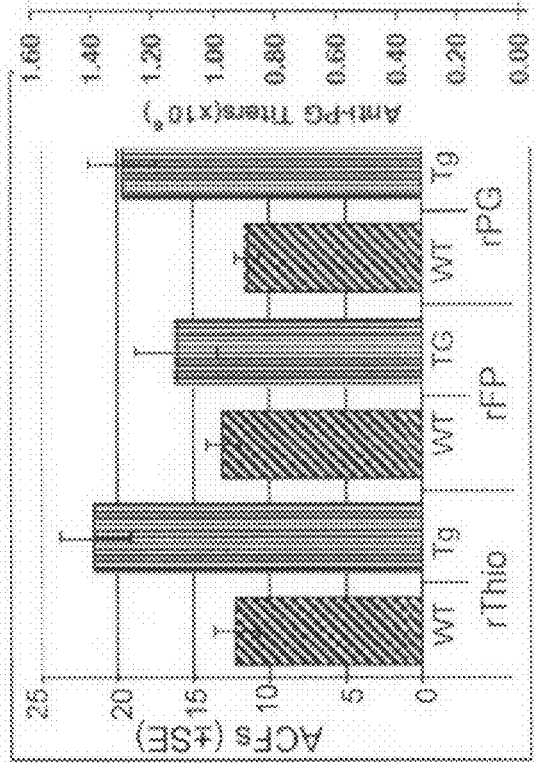
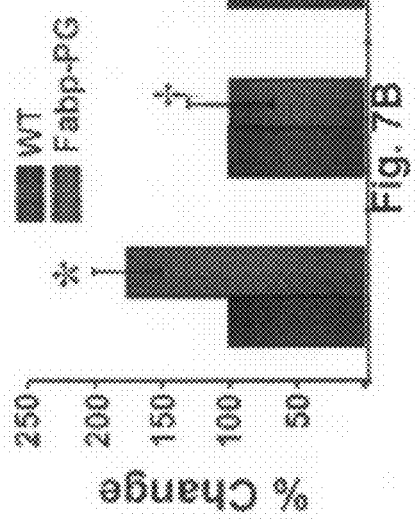
Fig. 7A
Fig. 7B
Fig. 7C

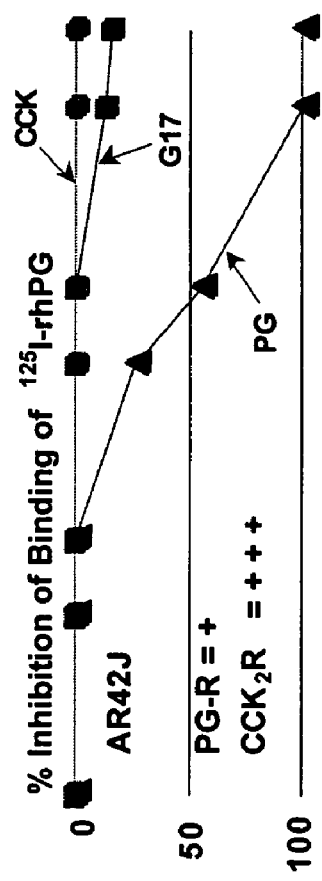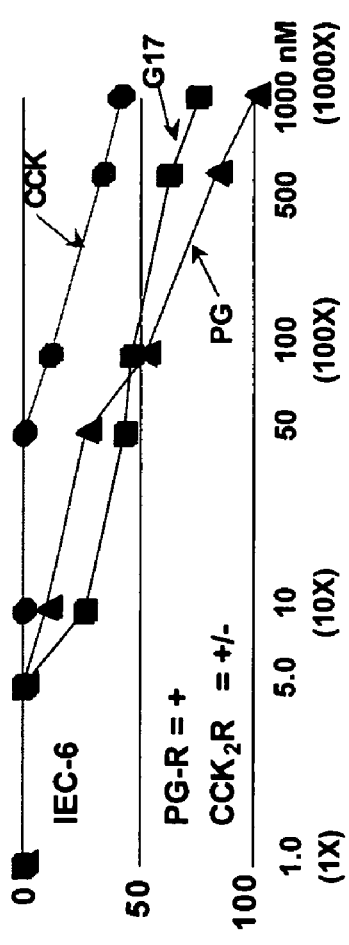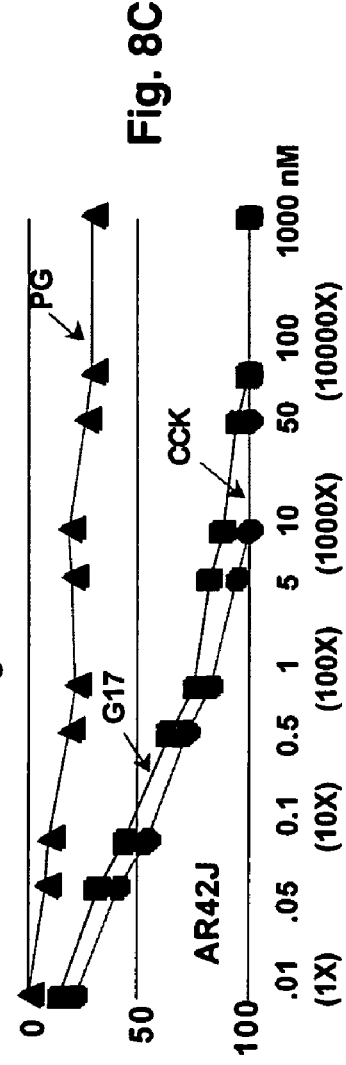

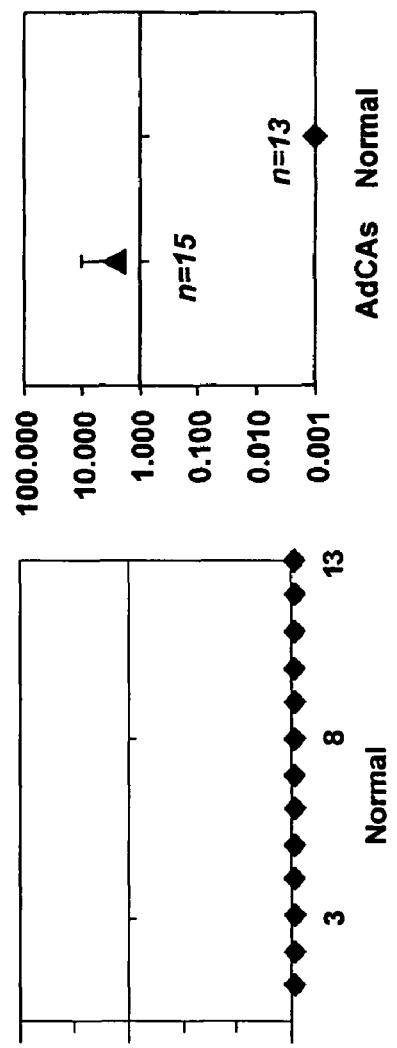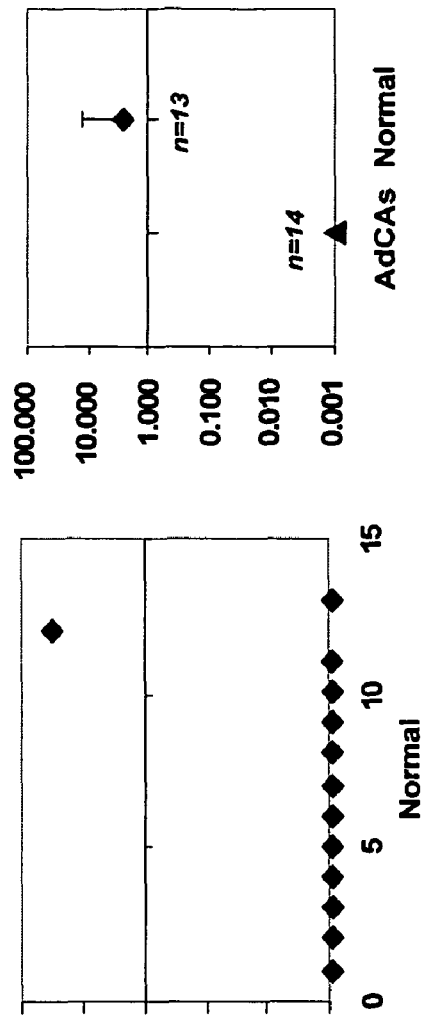
Fig. 9A
Fig. 9C

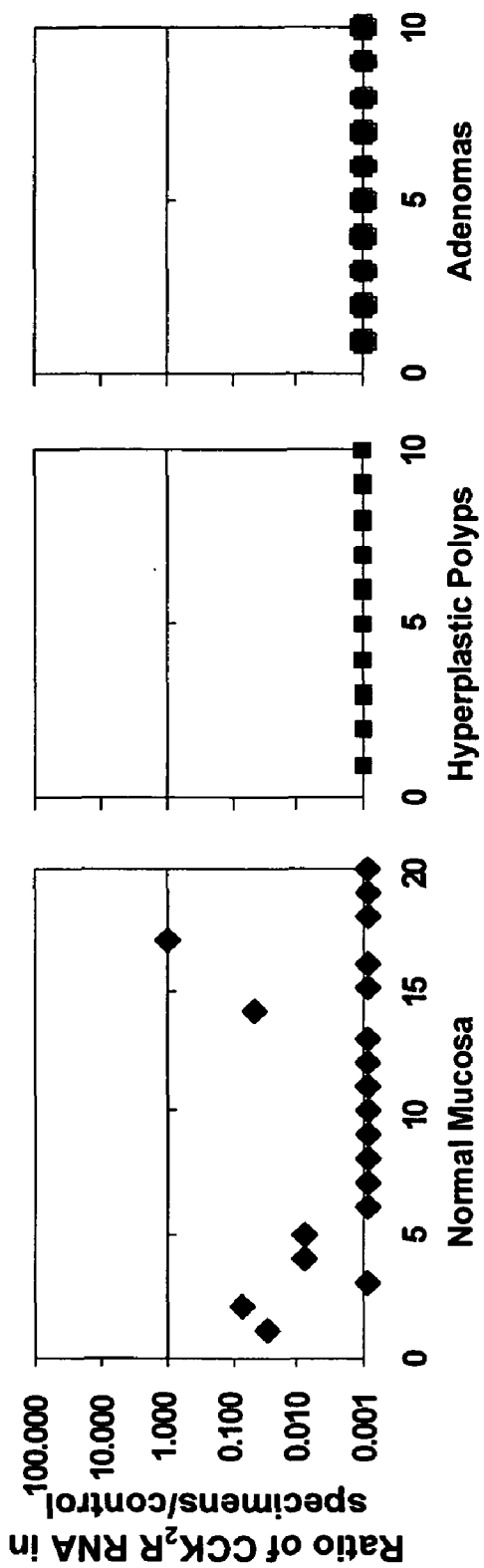
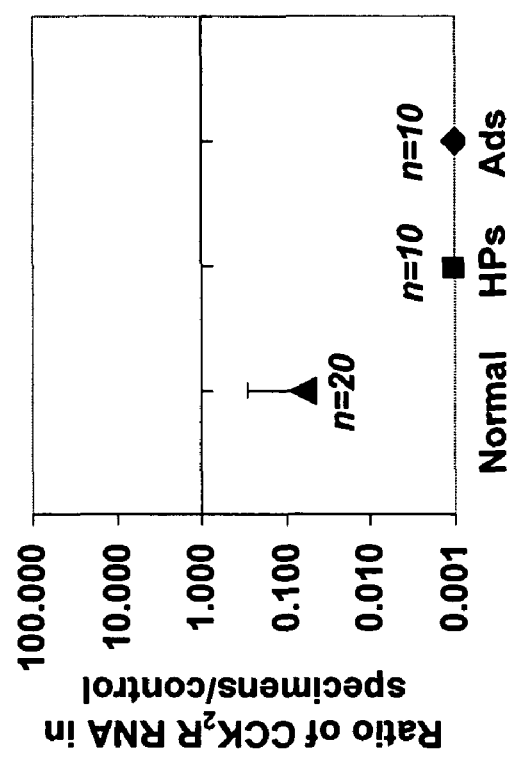
Fig. 9B

HGP-CDS (SEQ ID NO: 1)

```
tcttgaagc  ccgctccca  gcagccagat  gcacccttag  gtacaggggc   50
caacaggac  ctggagctac  cctggctgga  gcagcagggc  ccagcctctc  100
atcatcgaag  gcagctggga  ccccagggtc  ccccacacct  cgtggcagac  150
ccgtccaaga  agcagggacc  atggctggaa  gaagaagaag  aagcctatgg  200
atggatggag  ttcggccgcc  gcagtgctga  ggatgagaac              240
```

HGP-OPT (SEQ ID NO: 2)

```
tcttgaaaac  cgcgcagtca  gcaaccggat  gcaccactgg  gtacgggcgc   50
caaccgtgac  ctggaattac  cgtggcttga  acagcaaggc  ccagcctctc  100
atcatcgtcg  ccagctgggc  ccgcaaggtc  cacctcactt  agtggcggat  150
ccgtccaaaa  agcagggacc  atggctggaa  aggccctatgg             200
ttggatggat  ttcggccgcc  gtagtgcgga  agatgagaac              240
```

```
HGP-CDS:   1   tcttgaagcccgctcccagcagccagatgcacccttaggtacaggggccaacaggac    60
               ||||||||| ||||  |||||||||||||||| ||||||||||||||||||||||||
HGP-OPT:   1   tcttgaaaaccgcgcagtcagcaaccggatgcaccactgggtacgggcgccaaccgtgac   60

HGP-CDS:  61   ctggagctaccctggctggagcagcagggcccagcctctcatcatcgaaggcagctggga  120
               ||||| | ||| |||| |||| |||| ||||| ||||||||||||||| ||||||||| 
HGP-OPT:  61   ctggaattaccgtggcttgaacagcaaggcccagcctctcatcatcgtcgccagctgggc  120

HGP-CDS: 121   ccccagggtcccccacacctcgtggcagacccgtccaagaagcagggaccatggctgag   180
               ||||||||| |  ||||| |||||| || ||||||||| |||||||||||||||||| 
HGP-OPT: 121   ccgcaaggtccacctcacttagtggcggatccgtccaaaaagcagggaccatggctggaa   180

HGP-CDS: 181   gaagaagaagaagcctatggatggatggagttcggccgccgcagtgctgaggatgagaac  240
               ||||||||| || ||||||||||||||   ||||||||||| ||||| ||||||||||
HGP-OPT: 181   gaggaagaagaaggcctatggttggatggatttcggccgccgtagtgcggaagatgagaac  240
```

Fig. 10C

Progastrin peptide:   Fig. 10D
Molecular weight: 9080.89 Daltons
  80 amino acids: 9 Strongly basic (+) amino acids (K, R), 14 strongly
Acidic (-) amino acids (D,E), 19 hydrophobic amino acids (A, I, L, F, W, V),
16 polar amino acids (N,C,Q,S,T,Y).
4.993 Isoelectric Point; -4.570 charge at pH 7.0.
Translate DNA sequence HGP-OPT: (% A+T=40.83; %C+G=59.17)

Codon usage:
gca Ala(A) 1 # cag Gln(Q) 4 # uug Leu(L) 0 # uaa Ter(.) 0
gcc Ala(A) 3 # --- Gln(Q) 7 # --- Leu(L) 7 # uag Ter(.) 0
gcg Ala(A) 2 # gaa Glu(E) 6 # aaa Lys(K) 2 # uga Ter(.) 0
gcu Ala(A) 0 # gag Glu(E) 3 # aag Lys(K) 1 # --- Ter(.) 0
--- Ala(A) 6 # --- Glu(E) 9 # --- Lys(K) 3 # aca Thr(T) 0
aga Arg(R) 0 # gga Gly(G) 1 # aug Met(M) 1 # acc Thr(T) 0
agg Arg(R) 0 # ggc Gly(G) 4 # --- Met(M) 1 # acg Thr(T) 1
cga Arg(R) 0 # ggg Gly(G) 0 # uuc Phe(F) 1 # acu Thr(T) 0
cgc Arg(R) 3 # ggu Gly(G) 3 # uuu Phe(F) 0 # --- Thr(T) 1
cgg Arg(R) 0 # --- Gly(G) 8 # --- Phe(F) 1 # ugg Trp(W) 4
cgu Arg(R) 3 # cac His(H) 1 # cca Pro(P) 4 # --- Trp(W) 4
--- Arg(R) 6 # cau His(H) 2 # ccc Pro(P) 0 # uac Tyr(Y) 0
aac Asn(N) 2 # --- His(H) 3 # ccg Pro(P) 5 # uau Tyr(Y) 1
aau Asn(N) 0 # aua Ile(I) 0 # ccu Pro(P) 1 # --- Tyr(Y) 1
--- Asn(N) 2 # auc Ile(I) 0 # --- Pro(P) 10 # gua Val(V) 0
gac Asp(D) 1 # auu Ile(I) 0 # agc Ser(S) 0 # guc Val(V) 0
gau Asp(D) 4 # --- Ile(I) 0 # agu Ser(S) 2 # gug Val(V) 1
--- Asp(D) 5 # cua Leu(L) 0 # uca Ser(S) 0 # guu Val(V) 0
ugc Cys(C) 0 # cuc Leu(L) 0 # ucc Ser(S) 1 # --- Val(V) 1
ugu Cys(C) 0 # cug Leu(L) 4 # ucg Ser(S) 0 # nnn ???(X) 0
--- Cys(C) 0 # cuu Leu(L) 1 # ucu Ser(S) 2 # TOTAL 80
caa Gln(Q) 3 # uua Leu(L) 2 # --- Ser(S) 5 #

Translate DNA Sequence HGP-CD:
% A+T = 37.08 [89],% C+G = 62.92 [151]

Codon usage:

| | | | | | |
|---|---|---|---|---|---|
| gca Ala(A) 2 | # cag Gln(Q) 7 | # uug Leu(L) 0 | # uaa Ter(.) 0 |
| gcc Ala(A) 3 | # --- Gln(Q) 7 | # --- Leu(L) 7 | # uag Ter(.) 0 |
| gcg Ala(A) 0 | # gaa Glu(E) 4 | # aaa Lys(K) 0 | # uga Ter(.) 0 |
| gcu Ala(A) 1 | # gag Glu(E) 5 | # aag Lys(K) 3 | # --- Ter(.) 0 |
| --- Ala(A) 6 | # --- Glu(E) 9 | # --- Lys(K) 3 | # aca Thr(T) 1 |
| aga Arg(R) 0 | # gga Gly(G) 3 | # aug Met(M) 1 | # acc Thr(T) 0 |
| agg Arg(R) 2 | # ggc Gly(G) 2 | # --- Met(M) 1 | # acg Thr(T) 0 |
| cga Arg(R) 1 | # ggg Gly(G) 1 | # uuc Phe(F) 1 | # acu Thr(T) 0 |
| cgc Arg(R) 3 | # ggu Gly(G) 2 | # uuu Phe(F) 0 | # --- Thr(T) 1 |
| cgg Arg(R) 0 | # --- Gly(G) 8 | # --- Phe(F) 1 | # ugg Trp(W) 4 |
| cgu Arg(R) 0 | # cac His(H) 1 | # cca Pro(P) 4 | # --- Trp(W) 4 |
| --- Arg(R) 6 | # cau His(H) 2 | # ccc Pro(P) 5 | # uac Tyr(Y) 0 |
| aac Asn(N) 2 | # --- His(H) 3 | # ccg Pro(P) 1 | # uau Tyr(Y) 1 |
| aau Asn(N) 0 | # aua Ile(I) 0 | # ccu Pro(P) 0 | # --- Tyr(Y) 1 |
| --- Asn(N) 2 | # auc Ile(I) 0 | # --- Pro(P) 10 | # gua Val(V) 0 |
| gac Asp(D) 3 | # auu Ile(I) 0 | # agc Ser(S) 0 | # guc Val(V) 0 |
| gau Asp(D) 2 | # --- Ile(I) 0 | # agu Ser(S) 1 | # gug Val(V) 1 |
| --- Asp(D) 5 | # cua Leu(L) 1 | # uca Ser(S) 0 | # guu Val(V) 0 |
| ugc Cys(C) 0 | # cuc Leu(L) 1 | # ucc Ser(S) 2 | # --- Val(V) 1 |
| ugu Cys(C) 0 | # cug Leu(L) 4 | # ucg Ser(S) 0 | # nnn ???(X) 0 |
| --- Cys(C) 0 | # cuu Leu(L) 0 | # ucu Ser(S) 2 | # TOTAL 80 |
| caa Gln(Q) 0 | # uua Leu(L) 1 | # --- Ser(S) 5 | # |

Fig. 10E

SWKPRSQQPDAPLGTGANRDLELPWLE
QQGPASHHRRQLGPQGPPHLVADPSKK
QGPWLEEEEEAYGWMDFGRRSAEDEN  (SEQ ID NO: 3)

Fig. 10G

Codon usage table for Escherichia coli [gbbct]:

10136 CDS's (3178987 codons)

fields: [triplet] [frequency: per thousand] ([number])
UUU 21.9( 69602) UCU 9.9( 31545) UAU 16.9( 53812) UGU 5.1( 16247)
UUC 16.4( 52096) UCC 9.1( 28810) UAC 12.3( 39072) UGC 6.2( 19685)
UUA 13.9( 44202) UCA 8.1( 25833) UAA 2.0( 6407) UGA 0.9( 2960)
UUG 13.1( 41565) UCG 8.6( 27301) UAG 0.2( 773) UGG 13.9( 44264)
CUU 11.2( 35750) CCU 7.2( 22849) CAU 12.6( 39927) CGU 20.6( 65571)
CUC 10.3( 32863) CCC 5.1( 16358) CAC 9.6( 30485) CGC 20.6( 65580)
CUA 4.0( 12657) CCA 8.6( 27274) CAA 14.7( 46673) CGA 3.5( 11277)
CUG 50.4(160178) CCG 22.0( 69849) CAG 28.6( 90827) CGG 5.4( 17092)
AUU 30.1( 95737) ACU 10.0( 31846) AAU 19.2( 60969) AGU 9.2( 29358)
AUC 24.4( 77713) ACC 22.8( 72577) AAC 21.8( 69150) AGC 15.3( 48691)
AUA 5.6( 17743) ACA 8.2( 26150) AAA 34.8(110660) AGA 2.8( 8968)
AUG 26.8( 85301) ACG 13.8( 43743) AAG 11.5( 36583) AGG 1.7( 5254)
GUU 19.6( 62243) GCU 16.8( 53363) GAU 32.6(103749) GGU 25.9( 82424)
GUC 14.6( 46398) GCC 24.5( 77968) GAC 19.5( 61897) GGC 28.4( 90131)
GUA 11.4( 36391) GCA 21.0( 66655) GAA 39.7(126105) GGA 8.7( 27638)
GUG 25.2( 80242) GCG 31.8(101140) GAG 18.2( 57805) GGG 11.0( 35011)
Coding GC 51.11% 1st letter GC 58.33% 2nd letter GC 40.69%
3rd letter GC 54.31%

Fig. 10F

IMMUNOGENIC COMPOSITIONS COMPRISING PROGASTRIN AND USES THEREOF

CROSS REFERENCE TO RELATED APPLICATION

This non-provisional application claims benefit of provisional application U.S. Ser. No. 60/875,732 filed on Dec. 19, 2006, now abandoned.

FEDERAL FUNDING LEGEND

This invention was produced using funds obtained through a National Institutes of Health grant (R01 CA097959). Consequently, the Federal government has certain rights in this invention.

BACKGROUND OF THE INVENTION

1. Field of the Invention

The present invention relates generally to the field of immunology and vaccine development. More specifically, the present invention provides various immunogenic compositions comprising progastrin and their use in the prevention and treatment of cancer.

2. Description of the Related Art

Colorectal cancers are one of the most common forms of cancers in men and women in the US and one of the leading causes of death. The sequence of genetic events that are associated with the multi-step process of developing different types of familial colon cancers are well-known. Although advances in molecular genetics have led to better risk assessment and earlier diagnosis of colorectal cancer, it still remains a deadly disease for majority of the patients due to lack of effective adjuvant treatments. Such adjuvant or systemic treatments are likely to arise from a better understanding of factors that regulate proliferation of colonocytes and colon cancer cells. Just as genetic instability due to the inheritance of specific genetic defects plays a dominant role in initiation and progression of familial cancers, hyperproliferation is likely to play a permissive role in the initiation and progression of sporadic cancers. Hence, hyperproliferation is recognized as a risk factor that can initiate dysplastic growth, resulting in accumulation of genetic defects and progression to colon cancer. Gastrins represent a group of growth factors that can potentially play a prominent role in proliferation of normal and cancerous intestinal cells.

The gastrin gene is normally expressed and processed in the brain and in the antral stomach of mammalian species. The full length progastrin (PG) peptide (80 amino acids) undergoes enzymatic deletions both at the C and N terminal ends, to finally generate the fully processed C-terminally amidated gastrin peptides in the neuro endocrine cells (FIG. 1A). G17 and G34 amino acid gastrin peptides stimulate acid secretion and growth of the gastrointestinal (GI) tract. Although the colon cancer cells express the gastrin gene, they do not process the progastrin peptides (Singh et al., 2000a; Rengifo-Cam and Singh, 2004). Thus, patients with colorectal cancers (CRCs) are positive for significant levels of progastrin-like peptides in the circulation. Some studies have reported the presence of elevated levels of progastrin peptides but not gly-extended gastrin or gastrins in patients with colorectal cancers (Siddheshwar et al., 2001).

Additionally, a significant percentage of human colon cancer (HCC) cells have also been shown to require the expression of progastrin-like peptides for maintaining the in vitro and in vivo growth of the cells (Singh et al., 1996). Down-regulation of the gastrin gene resulted in the attenuation of the growth of gastrin dependent human colon cancer cells in vitro and in vivo (Singh et al., 1996). A processing intermediate, gly-extended gastrin (GG) was reported to exert potent growth factor effects on several target cells including normal and cancerous intestinal epithelial cells (IEC) (Seva et al., 1994; Singh et al., 1995). Additionally, U.S. Pat. No. 5,786,213 and U.S. Pat. No. 6,165,990 disclose gene therapy of colorectal cancers using the anti-sense technology. However, the delivery of the anti-sense plasmids has not advanced significantly and has remained a concern along with associated side effects.

The use of immunotherapy, on the other hand, has advanced significantly and is currently being used for treatment purposes of many cancers by targeting other cancer-related molecules such as EGF receptors, HER-2 Neu Oncogene, Anti CD52, anti VEGF, Anti CD22, Anti CD80 etc. (Rosenberg et al., 2004). A vaccine against the gastrin peptide (G17DT) was developed and has been used in clinical trials with ambiguous results (He and Marshall, 2006). The G17DT vaccine is a chemical conjugate of 9 N-terminal amino acids of G17 sequence conjugated to DT (Diptheria Toxin). Since it is difficult to have a uniform conjugate with similar composition and stoichiometric ratios of peptide to carrier, the immune response would vary from batch to batch of vaccine. Additionally, peptide vaccines produce limited immune response. Another problem with the DT vaccine is that it may produce immunosuppression against the DT-peptide sequences as most of the humans are immunized against Diptheria. Furthermore, the quality control and quality assurance of conjugate vaccine is difficult.

It is known that several receptor (R) sub-types mediate the biological functions of gastrin-like peptides and progastrin-like peptides. Of these, $CCK_2R$ and its splice variants mediate biological effects of primarily CCK and gastrin-like peptides. On the other hand, novel proteins such as Annexin II mediate growth factor effects of progastrin-like peptides (Singh et al., 2007). The G17 N-terminal based vaccine essentially targets G17 and thus inhibits binding to CCK2R; progastrin based vaccine, on the other hand, may target the actions of progastrin peptides and inhibit binding to receptors such as Annexin-II. This may explain the high efficacy of the current vaccine.

Thus, prior art is deficient in an immunogenic composition that can be useful as vaccine in the treatment of cancers that produce progastrin ectopically or are dependent on progastrin for their growth. The current invention fulfils this long standing need in the art.

SUMMARY OF THE INVENTION

In one embodiment of the present invention, there is provided a composition comprising an agent targeting progastrin or an agent targeting annexin II or both of the agents. The agent comprises progastrin or a fragment thereof, an antibody directed against the progastrin or the fragment thereof or the progastrin or specific siRNA targeting gastrin gene. The agent targeting annexin II comprises an antibody directed against annexin II, annexin II specific siRNA or annexin II specific antisense oligonucleotide. The agents described herein may be formulated in a pharmaceutically acceptable adjuvant, a delivery system or a combination thereof.

In a related embodiment of the present invention, there is provided a method of inhibiting proliferation of a neoplastic cell. This method comprises contacting the neoplastic cell with the composition discussed supra. The composition may comprise either an agent that targets progastrin or an agent that targets annexin II or both. Such a contact inhibits the growth-inducing activity of progastrin in the cell, thereby inhibiting the proliferation of the neoplastic cell.

In another related embodiment of the present invention, there is provided a method of treating a cancer in an individual. This method comprises administering a pharmcologically effective amount of the composition discussed supra. The composition may comprise either an agent that targets progastrin or an agent that targets annexin II or both. Such administration inhibits gastrin-induced proliferation of cancer cell, thereby treating the cancer in the individual.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A shows processing of gastrins. FIG. 1B shows peptide structure of G17 in relation to that of recombinant human progastrin. The recombinant purified hPG (rhPG) was detected by Western immunoblot Analysis using specific anti-hPG-antibodies (Abs). The 21 kDa band represents the fusion protein (FP) used for expressing rhPG in an $E.\ coli$ system. The molecular markers co-run in Lane 1. Specificity of antibodies for detecting G17 and hPG was also examined. Gastrin-like peptides (G17, glycine-extended gastrin (GG), cholecystokinin (CCK-8) and hPG) were detected in a slot blot assay using anti-G17-Abs or anti-hPG Abs. Anti-G17-Ab was specific for G17 and did not detect other gastrin-like peptides to any significant extent. Similarly, anti-hPG-Ab was specific for progastrin-like peptides and did not detect any other gastrin-like peptide.

FIGS. 3A-3B show immunohistochemical staining of tumors from patients with adenocarcinoma. FIG. 3A shows immunohistochemical staining of tumors from patients with adenocarcinomas with an antibody directed against progastrin (PG-Ab). Sections of adenocarcinomas and hyperplastic/dysplastic colonic crypts from several patients was analyzed for the presence of progastrin peptide, histochemically with the progastrin-Ab. Adjacent normal colonic crypt samples from the same patient were also stained with progastrin-Ab. Representative data from one patient is shown. Normal colonic crypts were negative for staining while several dysplastic crypts stained significantly. Almost all adenocarcinomas were heavily stained. FIG. 3B shows immunofluorescent staining of representative human patient samples from adenomatous polyps and adenocarcinomas with either PG-antibodies or Annexin II-antibodies. The staining of PG-antibodies and Annexin II-antibodies was detected by using secondary antibodies that were tagged with either Texas Red or FITC-Green fluorescent dyes, as shown. In normal colonic (N. Colon) and Adenoma samples from patients, PG was detected with FITC green labeled second antibody, and Annexin —II staining was detected with Texas red labeled second antibody. But in adenocarcinoma samples from patients, PG staining was detected by Texas red tagged antibody and Annexin-II staining was detected by FITC-Green labeled antibody. The in situ binding of PG with Annexin II was established in the merged images showing yellow staining (FIG. 3B). The relative levels of progastrin and Annexin II and the relative co-localization (binding) of PG with ANX-II in 4-5 patient samples from normal mucosa, adenomas and adenocarcinomas are presented in Table II.

FIG. 4A-4F show that PG-R (Annexin II) plays an important role in the progastrin gene dependent cancers. FIG. 4A shows a hypothetical model depicting relative binding of progastrin (PG), G17 and CCK8 to $CCK_2$—R and PG-R (Annexin II) binding sites and resultant biological effects, based on published findings from our group as described elsewhere. FIG. 4B shows in vitro binding of Annexin II with PG peptides, where incubation of recombinant Annexin II and progastrin, in vitro, resulted in co-immunoprecipitation of the ligand and its receptor, as detected in Western Blots in the left hand panel and by coomassie blue in the right hand panel. FIG. 4C shows in situ binding of Annexin II with progastrin in colon cancer cells, expressing progastrin peptide (HCT-116 cells). FIG. 4C (panel ia) shows the presence of progastrin binding proteins of molecular mass of ~80 KDa, (band a), 40-50 KDa (band b) and ~36 KDa (band c). The proteins in band c were identified as annexin-II as shown in panel ib. Using pull-down assays in FIG. 4C (panel ic), with progastrin-antibody, Annexin II co-immunoprecipitated with progastrin from the cellular lysates of a representative colon cancer cell line, HCT-116, and was detected by Western Blot analysis. Using immunofluorescence in FIG. 4C (panel ii), progastrin was found to co-localize very strongly with Annexin II in HCT-116 cells, in situ, confirming a strong binding of PG with Annexin II in situ. In this figure, red flourescense depicts PG, green fluoroscense depicts annexin II and blue depicts nuclei stained with DAP1. Merged yellow image depicts co-localization of PG and annexin-II in HCT-116 cells expressing autocrine PG. In FIG. 4C (panel iii) shows that PG strongly co-localized with Annexin II in the proximal (P) colonic crypts of transgenic (Tg) mice (Fabp-PG) over-expressing progastrin in the colonic crypts. In panel iii A of FIG. 4C, magnification of 20× was used, while in panel iiiB of FIG. 4C, magnification of 40× was used. Absence of PG expression in the distal (D) (data not shown) and proximal (P) colonic crypts of wildtype mice (WT) was confirmed. In panel iiiB of FIG. 4C, upper panel (i) depicts distal crypts from Tg mice and lower panel (ii) depicts merged images from proximal crypts of Tg mice. The data in FIG. 4C (panels i-iii) thus confirmed that Annexin II functions as an avid binding partner for progastrin peptides in vitro and in vivo.

FIG. 4D (panel i) show a critical need for Annexin II expression for measuring growth effects of progastrin on intestinal epithelial cells (i and ii) and colon cancer cells (Singh et al, 2007). Anti-sense clones of IEC-18 cells (FIG. 4D (panel i)), down-regulated for ANX-II expression, were non-responsive to progastrin (PG), compared to sense clones (FIG. 4D (panel ii)). However, both the sense and anti-sense clones were equally responsive to fetal calf serum (FCS). Similarly, HCT-116 cells down regulated for autocrine expression of annexin II, demonstrated a significant loss in the growth of the anti-sense clones in response to autocrine PG, compared to wildtype and sense clones (Singh et al, 2007). Treatment of intestinal epithelial cells (IEC-18) (FIG. 4E (panel i)) and pancreatic cancer cells, (AR42J) (FIG. 4E (panel ii)) with Annexin II antibodies, but not $CCK_2R$ antibodies, resulted in the attenuation of growth effects of progastrin, but not the growth effects of FCS. FIG. 4F, shows that Annexin II plays a critical role in the internalization of progastrin in the intestinal epithelial cells. Down-regulation of Annexin II expression using specific Annexin II siRNA, resulted in the loss of binding and internalization of progastrin in the IEC cells. Control, non-specific siRNA treatment had no effect. However, significant binding of annexin II was observed with PG, resulting in internalization of the receptor and ligand (Yellow merged image), within 10 minutes of PG treatment.

FIGS. 5A-5B show effect of antibodies on growth of HCT-116 cells in culture. Growth of cells was examined by an MTT assay. In FIG. 5A, growth of cells in response to 1% FCS was arbitrarily assigned a 0 level. A decrease or increase in growth was recorded as % change compared to levels seen in control (1% FCS stimulated) cells. FIG. 5B shows effect of increasing concentration of anti-PG-Ab. 1:500 dilution of anti-PG-Ab completely reduced the growth of FCS-stimulated levels to non-stimulated levels.

FIGS. 6A-6C show immune response induced by hPG-fusion protein (FP) immunogen in different mouse models. FIG. 6A shows PG-Ab titers in Balb/c mice that were immunized with hPG-fusion protein (FP) immunogen at the indicated time points. The immunized Balb/c mice were inoculated with mouse CA cells at week 10 and sacrificed at week 14 and the tumors in the mice were weighed. Control mice received adjuvant alone. The weight of the tumors is indicated by an arrow against Ab titer of each mouse in mgs. Tumor weights from 3 of 6 animals are presented. The weights were ~1530% lower than that in control mice (820-1000 mg). The mouse that demonstrated highest titers between weeks 8-12 had the smallest tumor which was necrotic compared to solid tumors in other mice. FIGS. 6B and 6C show effect of vaccination with rhPG-FP immunogen on colon carcinogenesis in FVB/N mice. FVB/N mice were immunized with the hPG-fusion protein (FP) immunogen by 3-4 weekly injections and the PG-Ab titers were measured as described for the Balb/c mice. Once the mice developed significant PG-Ab titers, the mice were treated with azoxymethane (AOM) and the total number and size of tumors measured after 6 months of AOM treatment. The number of tumors (FIG. 6B) and the tumor burden (FIG. 6C) is presented herein. *=p<0.05 vs control values. Control mice were immunized with adjuvant alone.

FIGS. 7A-7E show effect of hPG fusion-protein (FP) on colon carcinogenesis in transgenic PS21 Fabp-PG mice. FIG. 7A shows the total number of aberrant crypt foci (ACF) in either PS21 transgenic mice (over-expressing PG in the colon) or wild type (WT) mice as Mean ±SD values (n=10 mice/group) from a representative experiment. FIG. 7B shows the % change in the number of ACF/mouse colon in PS21 transgenic mice in groups that were vaccinated with either thioredoxin (Thio) alone, or fusion protein (FP) containing thioredoxin plus progastrin, or progastrin (PG) alone, compared to that in the corresponding WT mice, wherein the levels in WT mice were arbitrarily assigned 100% values. FIG. 7C shows anti-progastrin antibody titers in wild type and PS21 (Transgenic) mice after immunization with recombinant proteins: thioredoxin (Thio), thioredoxin-progastrin fusion protein (FP) and progastrin (PG). FIG. 7D shows anti-progastrin titers in transgenic mice (PS21) mice expressing human progastrin after immunization with recombinant proteins: Thioredoxin, Thioredoxin-progastrin fusion protein and progastrin. FIG. 7E shows anti-thioredoxin titers in wild type and PS 21 mice.

FIGS. 8A-8C show binding of $^{125}$I-rhPG and $^{125}$I-BH-CCK8 to a pancreatic cancer cell line, AR42J and intestinal epithelial cells (IEC). Cells were incubated with the indicated radio labeled ligand in the presence or absence of increasing concentrations of either CCK8, G17 or rhPG. The relative binding affinity of the gastrin like peptides for the specific binding sites for rhPG (FIGS. 8A and B) (Annexin II) and CCK8 (FIG. 8C) to $CCK_2R$ was calculated. Data in each point represents the mean values of triplicate measurements from a single experiment and is representative of 2 similar experiments. The intra-experimental variation for each data point was <5-10%. The nM concentration of each peptide used is presented in a log-scale on the x-axis; the excess unlabeled peptide used for displacing the binding of the radio labeled ligand is presented in parentheses. The % loss in the relative binding of the radio labeled ligand in the presence of the increasing concentrations of the indicated non-labeled peptide is presented on the y-axis. IEC cells lack $CCK_2R$ binding sites and therefore binding with radio-labeled CCK8 was not examined with these cells.

FIGS. 9A-9C show relative levels of human gastrin RNA and hCCK2R RNA. FIG. 9A shows relative levels of human gastrin RNA in frozen (discarded) samples of adenocarcinomas and surrounding normal mucosal tissues (obtained from a tissue bank at UTMB). The relative levels of gastrin RNA, on an average as measured in each sample or in all samples (mean ±SD) in that group are shown compared to that in an arbitrarily chosen normal control mucosal sample. FIG. 9B shows relative levels of hCCK2R RNA in freshly obtained (non-frozen) hyperplastic polyps and adenomas compared to that in the surrounding normal mucosa. The levels are presented in relation to that measured in an arbitrarily chosen normal colonic mucosal control sample. The values represent an average of triplicate measurements from a single sample or mean ±SD of the indicated number of samples/group. FIG. 9C shows relative levels of hCCK2R RNA in frozen (discarded) samples of adenocarcinomas and surrounding normal mucosal tissues, obtained from the tissue bank at UTMB. The values presented herein is either a mean of triplicate measurements from a single specimen or a mean SD of the indicated number of specimens/group. The relative levels of CCK2R RNA in each sample is presented as a ratio of that measured in an arbitrarily chosen control normal mucosal sample.

FIGS. 10A-10G show diagrammatic representation or sequences of the vectors or nucleic acid sequences encoding proteins or amino acid sequences of the proteins discussed herein. FIG. 10A is a diagrammatic representation of the expression vector (pET32), that was used for expressing hgastrin cDNA. The codons for hgastrin cDNA was optimized for expression in *E. coli* and cloned in pET32 at the NspV-HINDIII restriction sites. In FIG. 10B shows details of the pET32 vector. This vector was designed for cloning and high level expression of peptide sequences fused with the 109 amino acid thioredoxin, TRX.TAG™, protein. Cloning sites are available on this vector for producing fusion proteins which contain the cleavable His.tag sequences for detection and purification. FIGS. 10C-10F show the blast sequence of hgastrin cDNA, used for cloning into the expression plasmid. The nucleotide sequence for the native coding cDNA for human gastrin gene (and hence, PG) is shown in comparison to the sequence that was used after codon optimization. FIG. 10G shows the amino acid sequence of the progastrin peptide thus expressed by the recombinant expression vector.

DETAILED DESCRIPTION OF THE INVENTION

Figure 1A:
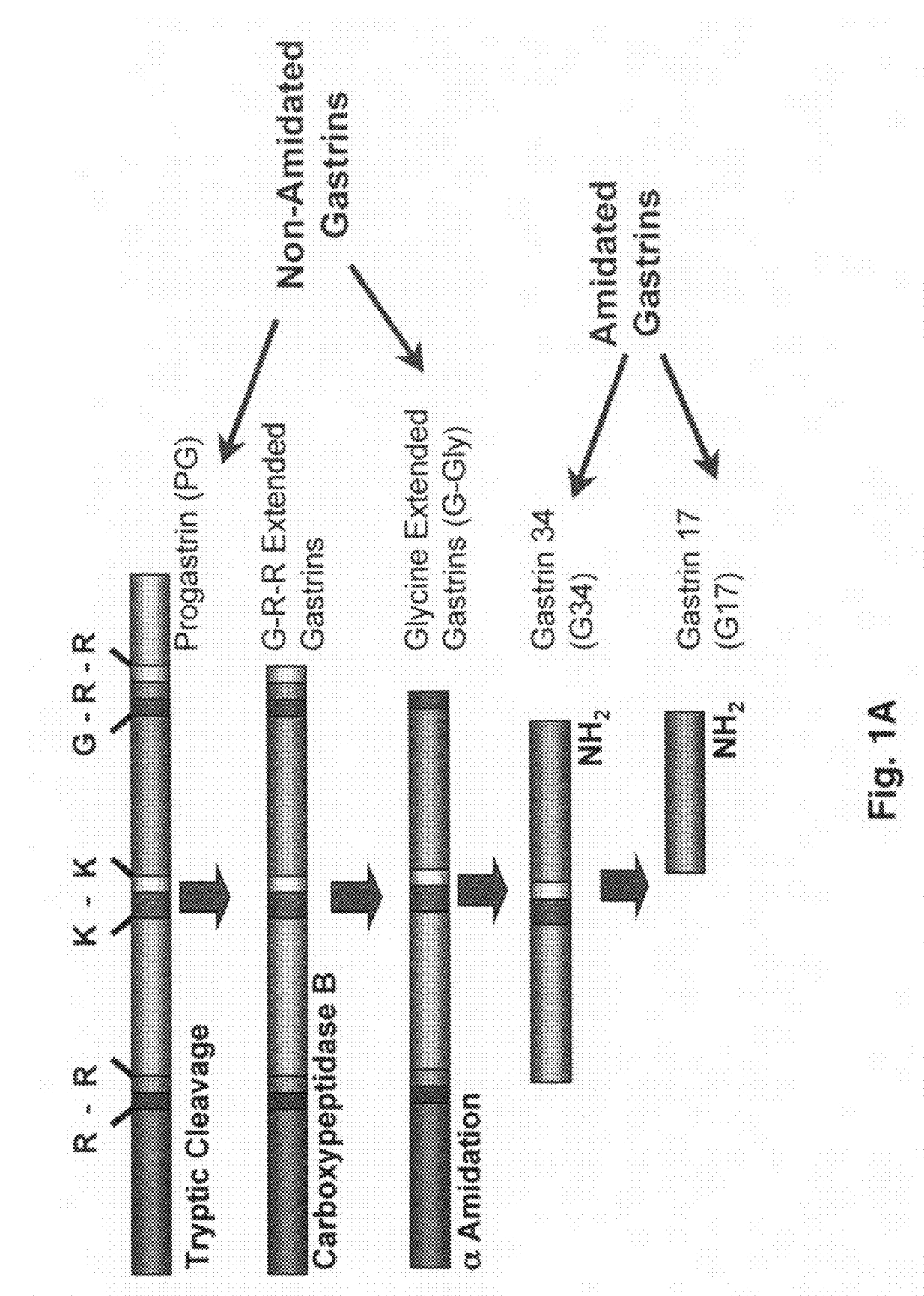
FIGS. 1A-1B are schematic representations of gastrin.

The present invention discloses immunogenic compositions comprising progastrin or a fragment thereof, a progastrin antibody, a progastrin siRNA, an annexin II antibody, an annexin II siRNA and their use in the treatment of cancers expressing the gastrin gene and the progastrin-like peptide. Progastrin and gastrin peptides are expressed in neuroendocrine cells in the brain and the antral part of the stomachs and processed into precursor peptide and glycine extended form of gastrins (GG). Additionally, subsequent amidation at the C-terminal end generates amidated forms of gastrins (G17, G24). Under physiological conditions, only processed forms of gastrins (G17, G34) are present as major circulating forms of gastrins (FIG. 1A).

Figure 1B:
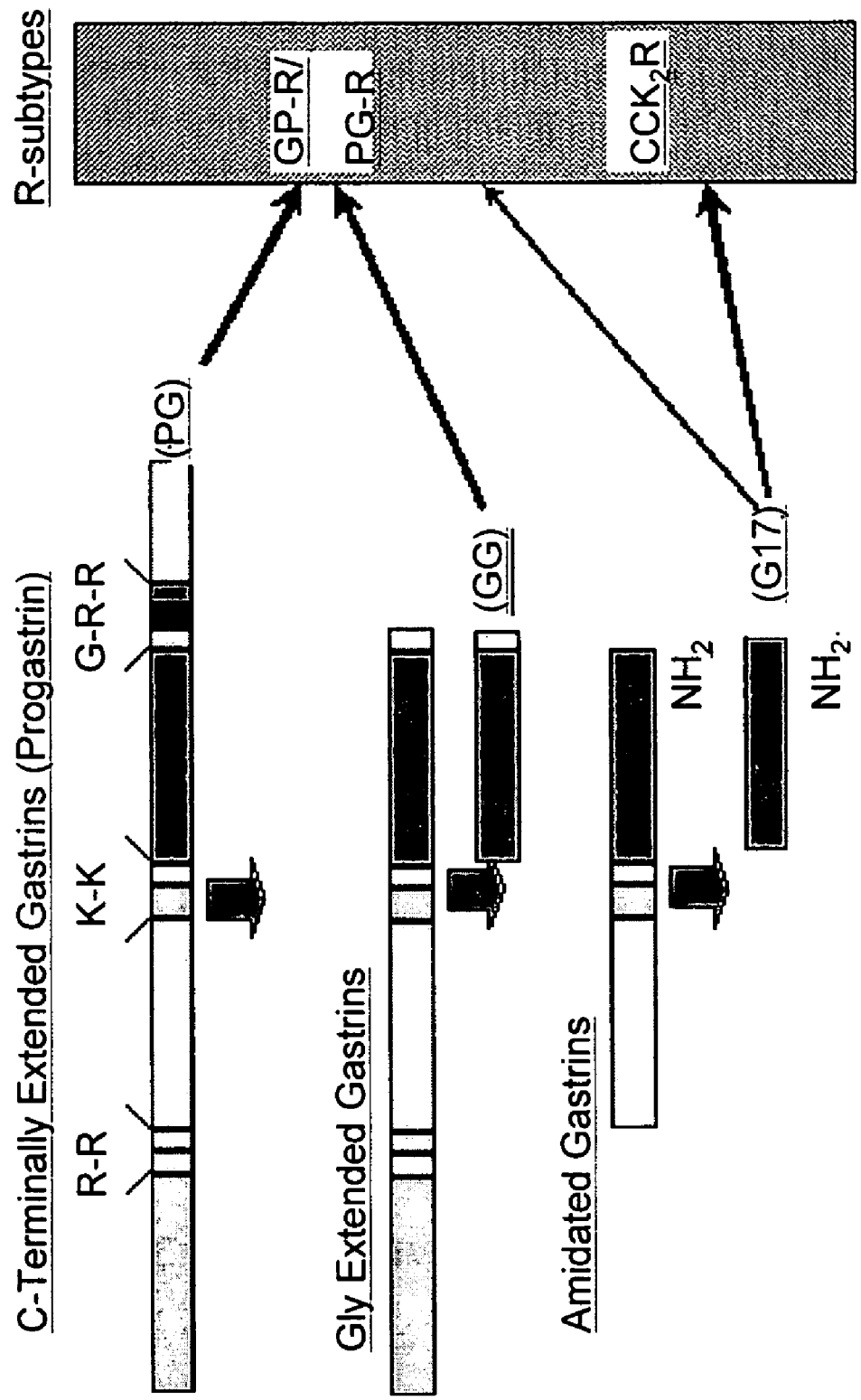
Figures 2A, 2B, 2C, 2D:
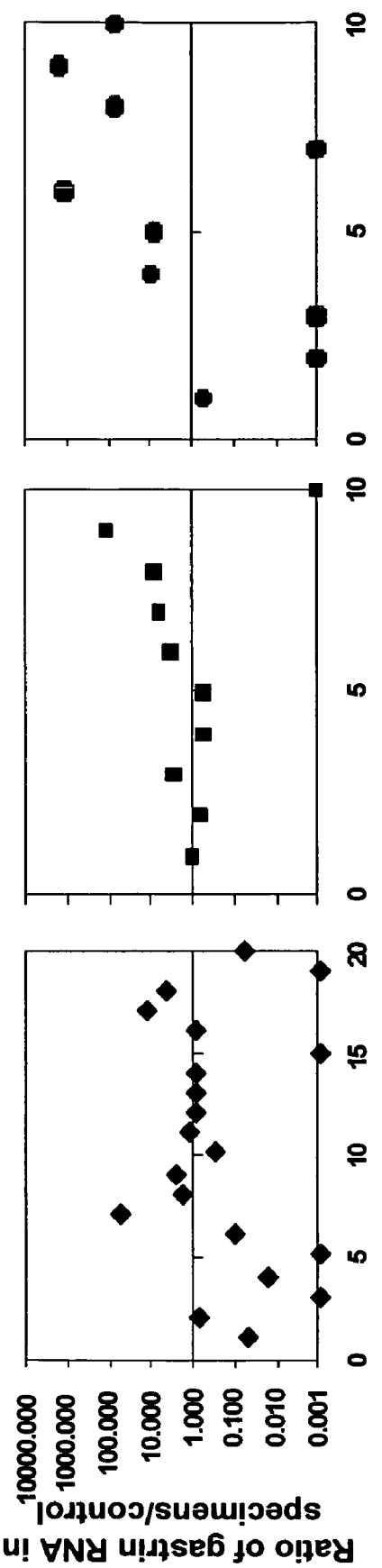
FIGS. 2A-2D shows relative levels of gastrin RNA in freshly obtained (non-frozen) hyperplastic polyps and adenomatous polyps compared to that in normal mucosa of the colon. The data is presented herein as a scatter plot wherein each value represents the relative levels of gastrin RNA in either each patient sample (FIGS. 2A-2C) or from all of the patients in that group (as mean ±SE) (FIG. 2D) compared to that in an arbitrarily chosen control normal mucosal sample.

The peptide structure of G17 and PG is diagrammatically presented in FIG. 1B. All antibodies derived against the C-terminal end of the peptides demonstrated specificity for the class of gastrin peptides since different forms of gastrin differ significantly from each other at the C-terminal end as shown in the western blot data in bottom right hand side in FIG. 1B. The anti-PG-Ab was very effective in detecting the 9 kDa molecule. Similarly dot blot assay in FIG. 1B shows that anti-PG-Ab specifically detected the presence of PG molecules but did not detect the presence of any other gastrin-like peptide. The anti-Gi7-Abs similarly were very specific for detecting amidated gastrins like G17, but did not detect GGly or rhPG-like molecules and did not detect a closely related amidated peptide, CCK-8. These antibodies can be used for immunohistochemical analysis (as disclosed herein), for measuring PG and G17 in the serum by either RIA or western blot analysis. The present invention also discloses that the gastrin gene was expressed at a very early stage during colon carcinogenesis in humans and that even hyperplastic polyps and adenomas express the gastrin gene and the PG-like peptides (FIGS. 2A-2D; Table 1).

TABLE 1

Gastrin gene expression in polyps relative to that in HCT-116 cells in relation to locus and pathology of polyps

|  | Count | Mean | Median | Std. Dev | Max |
|---|---|---|---|---|---|
| Locus |  |  |  |  |  |
| Proximal | 15 | 664.6512 | 0.136 | 2378.397 | 9247.3 |
| Transverse | 5 | 15948.96 | 38.7 | 35604.38 | 79640.0 |
| Distal | 1 | 5.36 | 5.36 |  | 5.36 |
| Rectum | 4 | 0.5034 | 0.327 | 0.5371101 | 1.25 |
| Pathology |  |  |  |  |  |
| Hyperplastic | 10 | 4.84706 | 0.1215 | 12.03971 | 38.7 |
| Microadenoma | 1 | 5.36 | 5.36 |  | 5.36 |
| Adenoma | 14 | 6436.636 | 7.695 | 21210.54 | 79640.0 |
| Adenocarcinoma | 1 | 0.54 | 0.54 |  | 0.54 |

Furthermore, staining of human adenomas and adenocarcinomas with anti-progastrin antibodies (FIG. 3A, 3B) corroborated the findings in FIGS. 2A-2D. A full length recombinant human PG peptide (rhPG) which was bioactive was generated recently and demonstrated potent growth factor-like effects of recombinant human PG peptide on intestinal epithelial cells (IEC), colon cancer cells and pancreatic cancer cells (Brown et al., 2003; Singh et al., 2003; Wu et al., 2003; Singh et al., 2007, Rengifo-Cam et al, 2007). The full length progastrin peptides are extended at both the N-terminal and C-terminal ends of the gastrin peptide (FIGS. 1A, 1B), which contributes to a significant difference in the receptor subtypes that bind PG peptides vs the gastrin peptides. Additionally, it is known that several receptor (R) sub-types mediate the biological functions of gastrin-like peptides and PG-like peptides. Of these, $CCK_2R$ and its splice variants mediate biological effects of primarily CCK and gastrin-like peptides. On the other hand, novel proteins such as Annexin II bind PG with high affinity (FIG. 4B, 4C), and mediate growth factor effects of PG-like peptides on colon cancer cells, intestinal epithelial cells and pancreatic cancer cells (FIGS. 4D and 4E) (Singh et al., 2007, Rengifo-Cam, 2007, Singh 2007).

It has also been suggested that gastrin-like peptides can mediate both stimulatory or inhibitory effects on the growth of target cells via $CCK_2R$. PG peptides, however, do not bind $CCK_2R$ and mediate only stimulatory effects on the growth of intestinal epithelial cells (IEC) and human colon cancer cells (HCC) via receptors other than CCK2R (Singh et al., 2007, Singh 2007, Rengifo-Cam et al 2007). Furthermore, studies with transgenic mice demonstrated that mice overexpressing PG and PG-like peptides were at an increased risk for colon carcinogenesis in response to chemical carcinogens (azoxymethane, AOM), while mice overexpressing gastrins were at reduced risk for colon carcinogenesis (Singh et al., 2000b; Singh et al., 2000c; Cobb et al., 2004). It was also suggested that while the presence of circulating PG-like peptides may function as a co-carcinogen and increase the risk for initiation of colon carcinogenesis, the presence of autocrine PG may further enhance the growth of the colorectal cancer tumors and progression of the disease. Thus, both circulating and autocrine progastrins can potentially play an important role in initiation and progression of colon cancer.

Figure 4A:
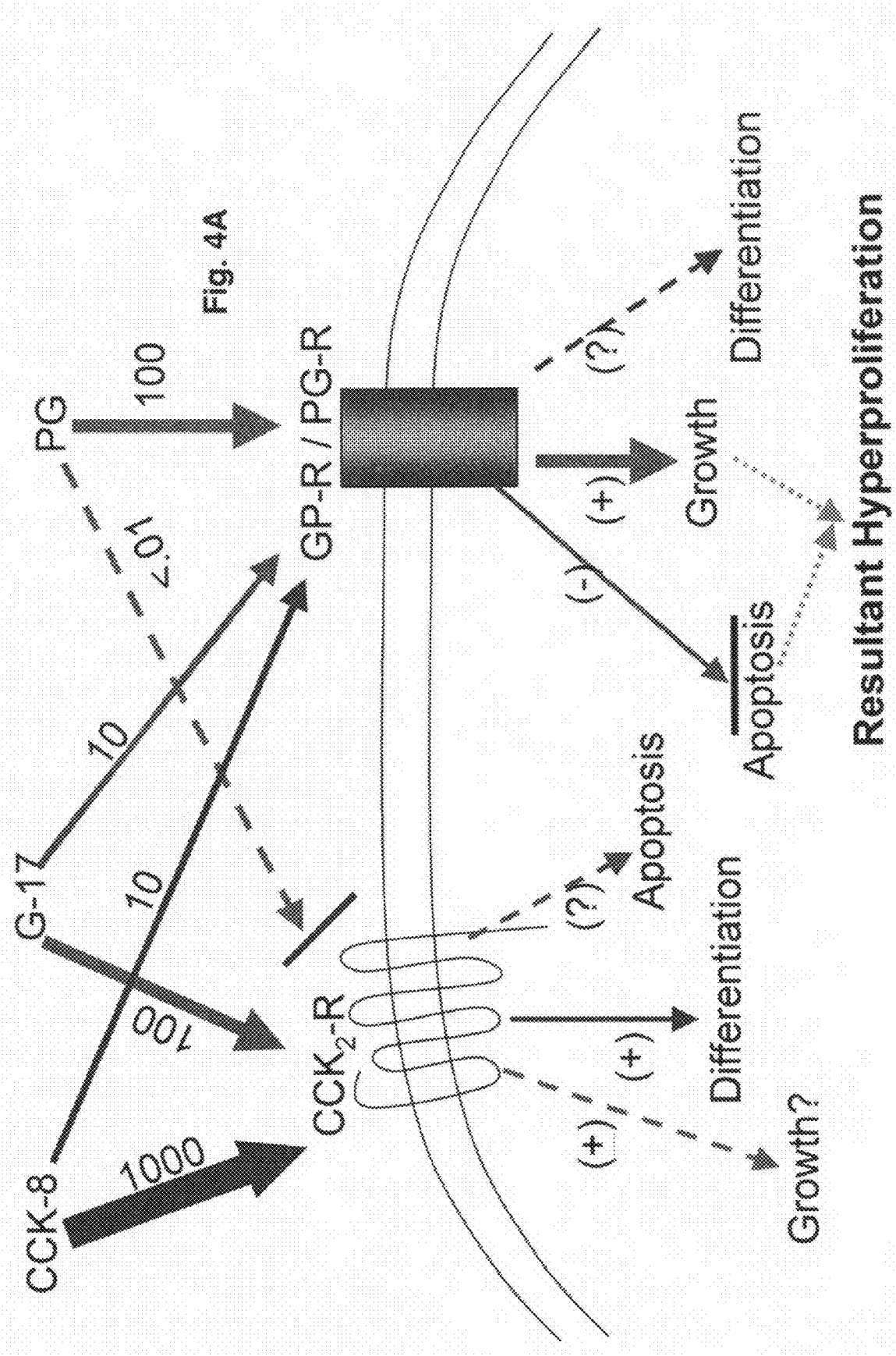
Figure 4B:
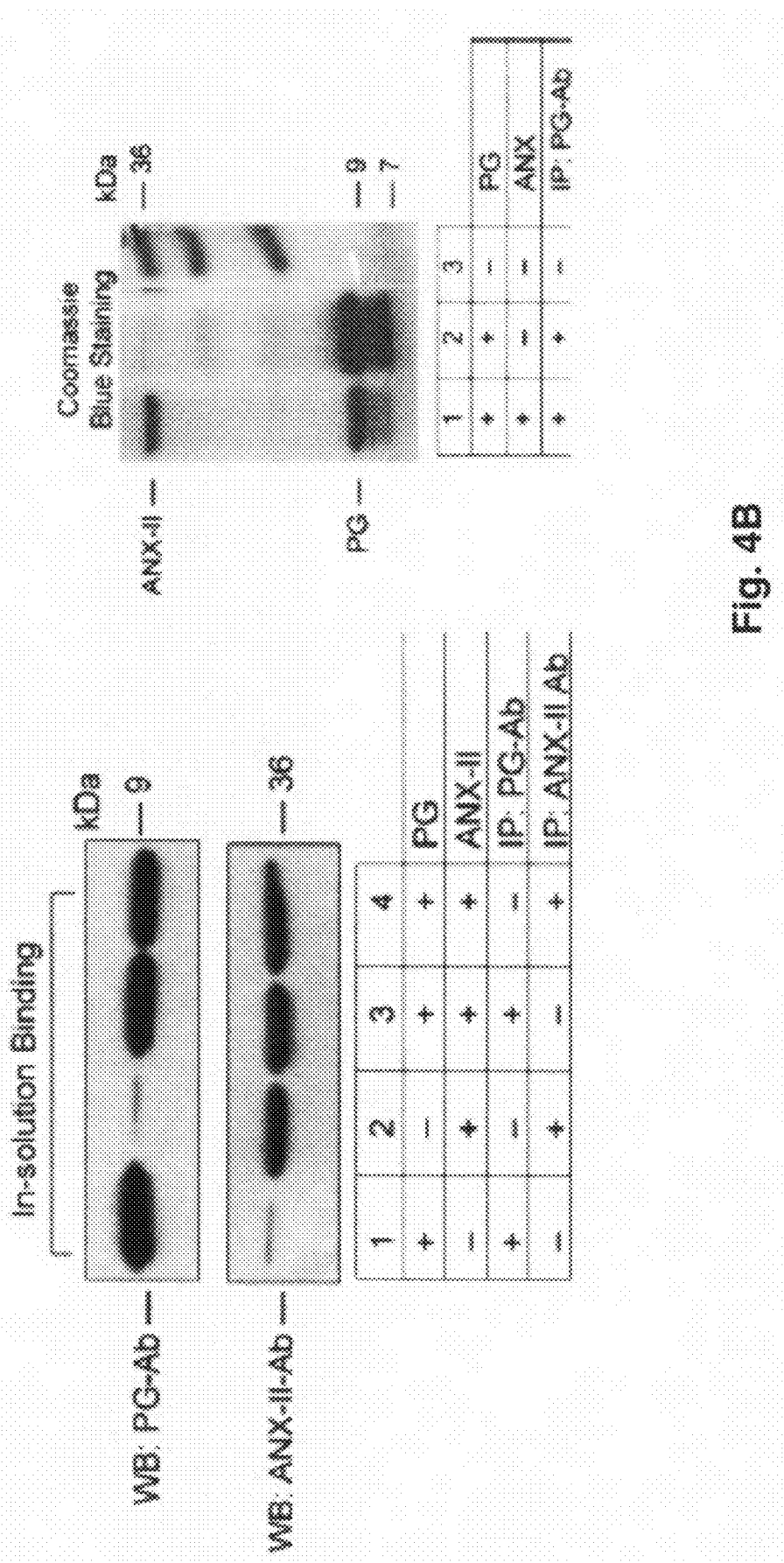
Figure 4C:
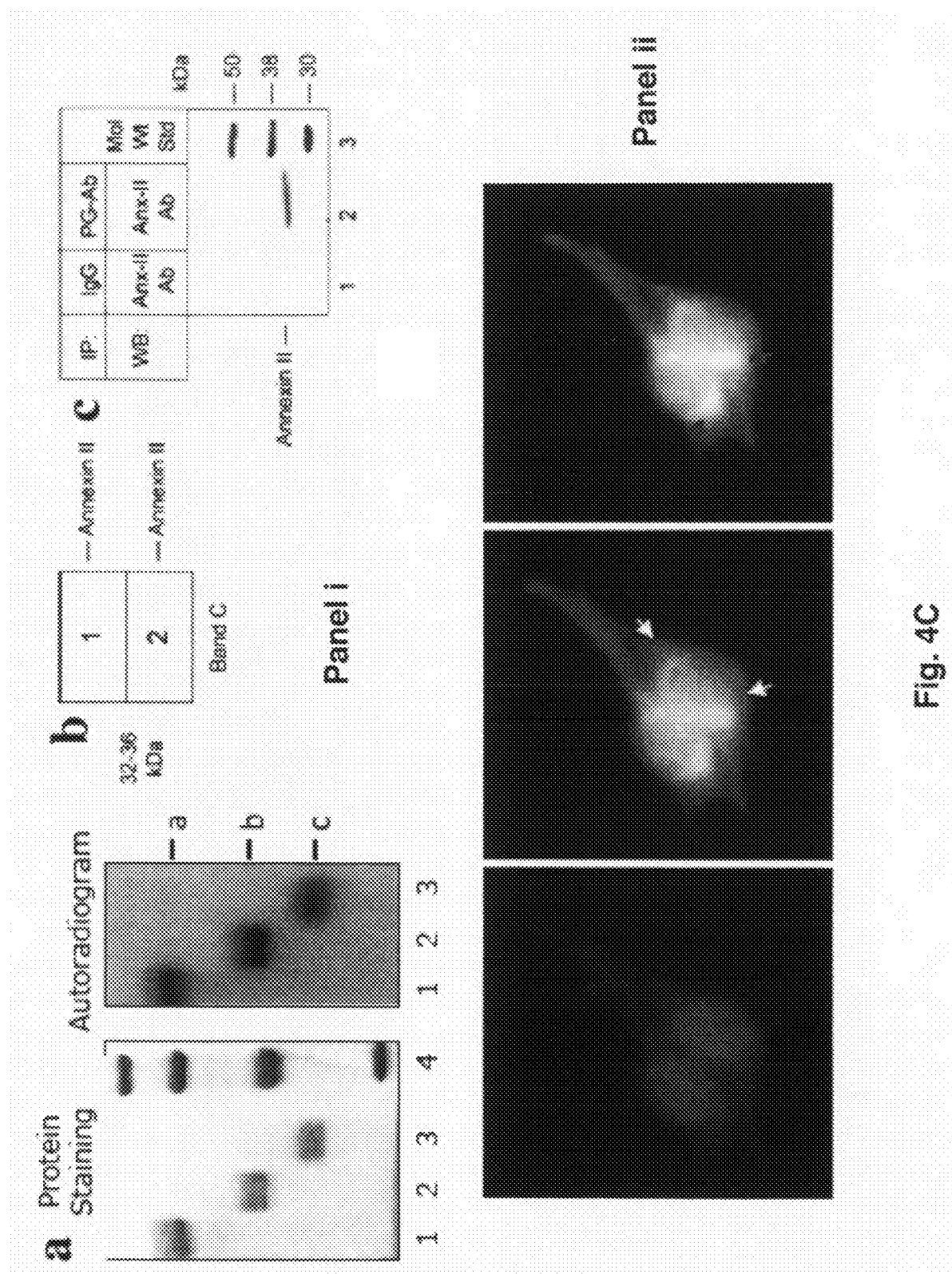
Figure 4C:
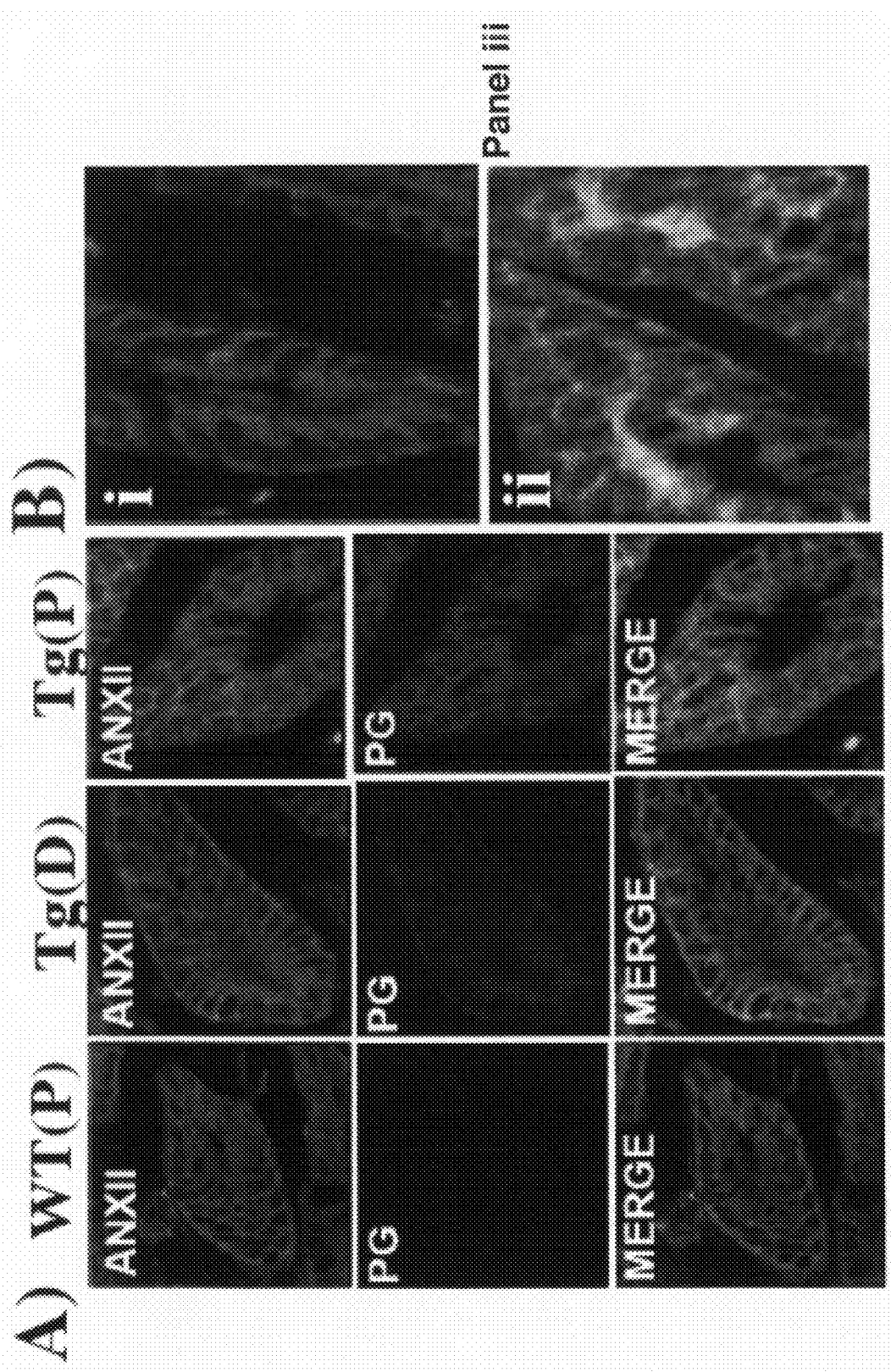
Figure 4D:
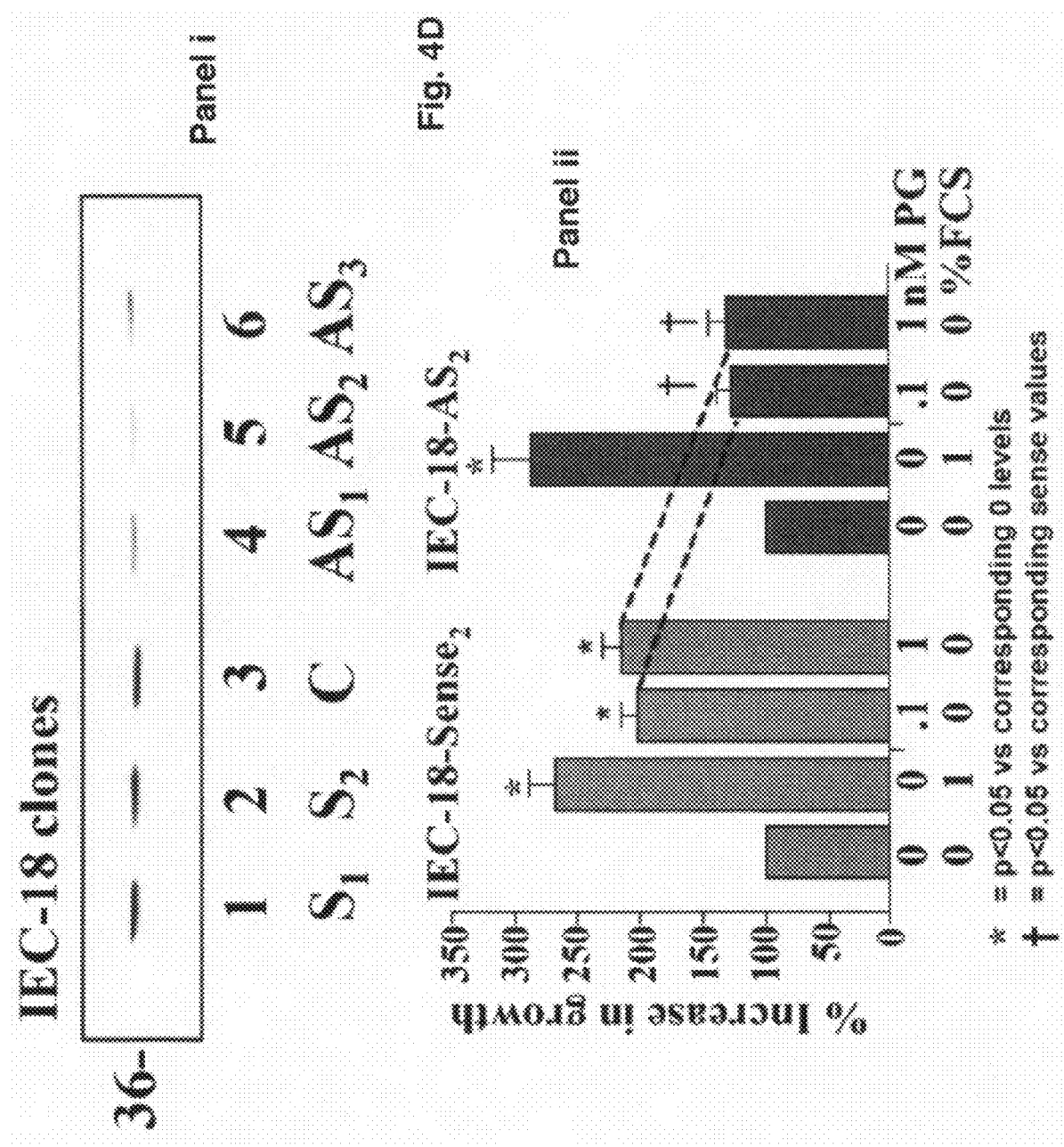

In summary, it was observed that, 1) gastrin peptides decrease rather than increase the risk of colon carcinogenesis, 2) both endocrine and autocrine progastrins increase the risk of colon carcinogenesis, and 3) colorectal cancer mainly express gastrin gene product, progastrin (FIG. 2-5), and the receptor Annexin II (FIG. 3B), but do not express amidated gastrins (FIG. 5) and CCK2R (FIG. 9B-C). Therefore, targeting progastrin and/or its receptor (Annexin II) rather than gastrins can be expected to be significantly more effective in inhibiting the growth of gastrin gene dependent colorectal tumors. A hypothetical model depicting relative binding of progastrin, G17 and CCK8 and PG-R (Annexin-II) binding sites and resultant biological effects is shown in FIG. 4A. Thus, differential expression of CCK2R and PG-R (Annexin II) on colonic mucosal cells may dictate co-carcinogenic vs protective effects of G17. Circulating progastrin was shown to promote proliferation and was co-carcinogenic on colonic mucosa in transgenic mice over-expressing hPG (hGAS and FABP-hGAS mice), but elevated levels of G17 in transgenic mice (INS-GAS) reduced the carcinogenic effects of AOM (Singh, et al, 2000 b and c; Singh et al 2004). The present invention demonstrates that antibodies against PG (FIG. 5) and/or Annexin II (FIGS. 4D, 4E) were most effective in attenuating the growth of gastrin gene-dependent human colon cancers in vitro whereas antibodies against gastrin peptides were completely ineffective (FIG. 5). This provides a strong evidence for potent growth promoting and co-carcinogenic role of autocrine progastrin on growth and tumorigenicity of gastrin gene-dependent colon cancer cells. Thus, developing auto-antibodies against progastrin-like peptides and/or Annexin II will reduce the risk of colon carcinogenesis and growth of colon cancer tumors in vivo.

A full length progastrin protein fused with a carrier protein, Thioredoxin (from bacteria) was examined herein as an effective vaccine against colon carcinogenesis in three animal models (Balb/C, FVB/N, FABP-PG). In these mouse models, the immunogen generated a strong response and very high titers of specific anti-hPG-Abs were measured within 4-8 weeks of vaccination. In the Balb/c mouse model, the potential effectiveness of the antigenic protein as a vaccine against the growth of a gastrin dependent mouse colon cancer cell line (CA) was observed (FIG. 6A). Mouse colon cancer cells are derived from Balb/c tumors and grow in Balb/C mice. Mouse PG shares ~80% homology at the C-terminal end and <65% homology at the N-terminal end with hPG. Colon cancer tumor weights in mice treated with hPG-immunogen were reduced 15-30% compared to that in control mice. Additionally, in one mouse that demonstrated the highest antibody titer, tumors were not only the smallest but also necrotic (FIG. 6A).

In the other mouse model, FVB/N mice were immunized against hPG-FP and treated with AOM to examine if anti-PG-Abs reduce the risk of colon carcinogenesis in these mice. The total number of tumors (FIG. 6B) and tumor burden/mouse (FIG. 6C) were significantly reduced (p<0.05) in mice immunized against hPG peptide compared to mice immunized with the adjuvant alone. In a third mouse model, FABP-PG where full length human progastrin would be an auto antigen in a transgenic mouse model expressing full length human progastrin, the fusion protein was used to test the ability of vaccine to elicit autologous immune response against progastrin. The progastrin fusion protein was able to elicit strong response in the transgenic as well as wild type mice. Progastrin alone was much less effective while thioredoxin was not effective at all (FIG. 7C). These results demonstrated that progastrin containing fusion protein was an effective vaccine against colon carcinogenesis in response to AOM.

Both tumorigenesis (FIGS. 6B and 6C) and pre-neoplastic markers of carcinogenesis, aberrant crypt foci, (FIGS. 7A & B) were significantly reduced in mice vaccinated with fusion progastrin protein, while mice vaccinated with either progastrin or thioredoxin alone showed no decrease in carcinogenesis. Aberrant crypt foci are reliable early markers of colon carcinogenesis and are used to predict tumorigenesis in rodent models and human patients (Takayama et al., 1998; Olivo and Wargovich, 1998). Thus, the results discussed supra provide strong evidence that the fusion protein could be used as an effective vaccine against either the initiation of colon carcinogenesis in patients positive for high levels of progastrin or can be used to significantly reduce the growth of gastrin-dependent cancers/tumors in patients.

It was demonstrated herein that relative levels of gastrin RNA was significantly lower in normal mucosa tissue than in frozen specimens of adenocarcinomas (FIG. 9A). Additionally, low to negligible levels of CCK2R RNA were detected in normal mucosa of patients from whom polyps were obtained. None of the polyps and adenomas expressed detectable levels of CCK2R (FIG. 9B). Furthermore, in the frozen adenocarcinoma samples and in the majority of surrounding normal colonic mucosal samples from these patients, no CCK2R RNA was measured (FIG. 9C). Only one normal mucosal sample was positive for CCK2R RNA. Thus, while the levels of gastrin RNA were higher in adenocarcinoma, the levels of $CCK_2R$ RNA were lower in such samples. This presence of lower levels of $CCK_2R$ in the normal colonic mucosa and the almost complete absence of $CCK_2R$ expression in the colonic tumors suggests that $CCK_2R$ does not play an important role in colon carcinogenesis. On the other hand, the high affinity receptors for progastrin, Annexin II, was increasingly expressed in colonic tumors in the order of adenocarcinomas>adenomas>normal colonic mucosa (FIG. 3B, Table II), further accentuating an important role of Annexin II and progastrin in colon carcinogenesis.

TABLE 2

Relative intensity of PG/ANXII staining and co-localization in normal colonic mucosa (N) and corresponding Ad and AdCA

| Sample | N | | Ad | | N | | AdCA | |
|---|---|---|---|---|---|---|---|---|
| | PG | ANXII | PG | ANXII | PG | ANXII | PG | ANXII |
| 1 | 0 | 0 | 0 | 0(0)[a] | 0 | 1 | 0 | 1(0)[a] |
| 2 | 0 | 0 | 0 | 1(0) | 0 | 1 | 0 | 2(0) |
| 3 | 0 | 1 | 2 | 1(1) | 0 | 1 | 3 | 4(3) |
| 4 | 0 | 1 | 3* | 3(3) | 0 | 2 | 4 | 4(4) |
| 5 | — | — | 0 | 2(0) | 0 | 3 | 5* | 5(5) |

(Scale of staining: 0-5 = low-high;
[a]= relative colocalization of PG and ANXII (yellow) is given in parentheses.
*= samples shown in FIG. 3B.

Figure 10A:
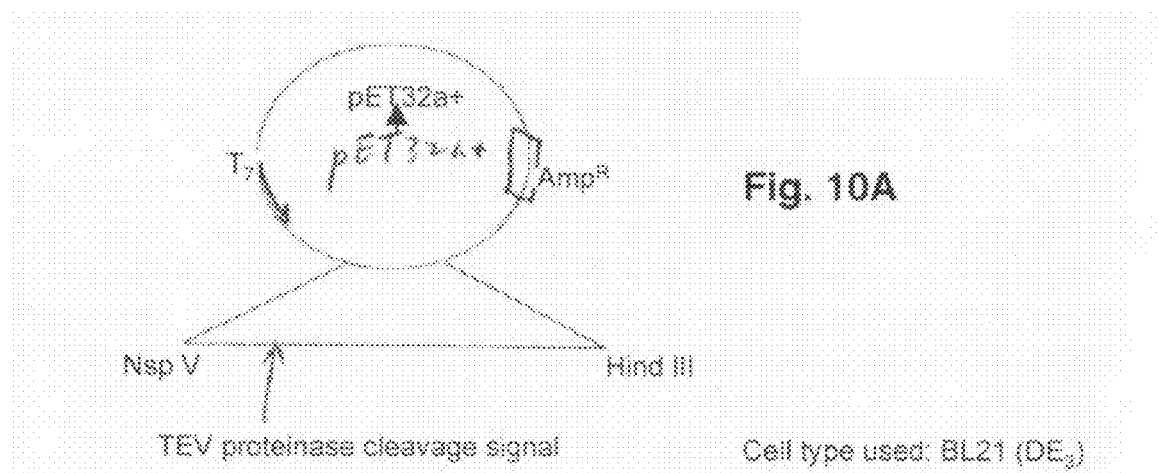
Figure 10B:
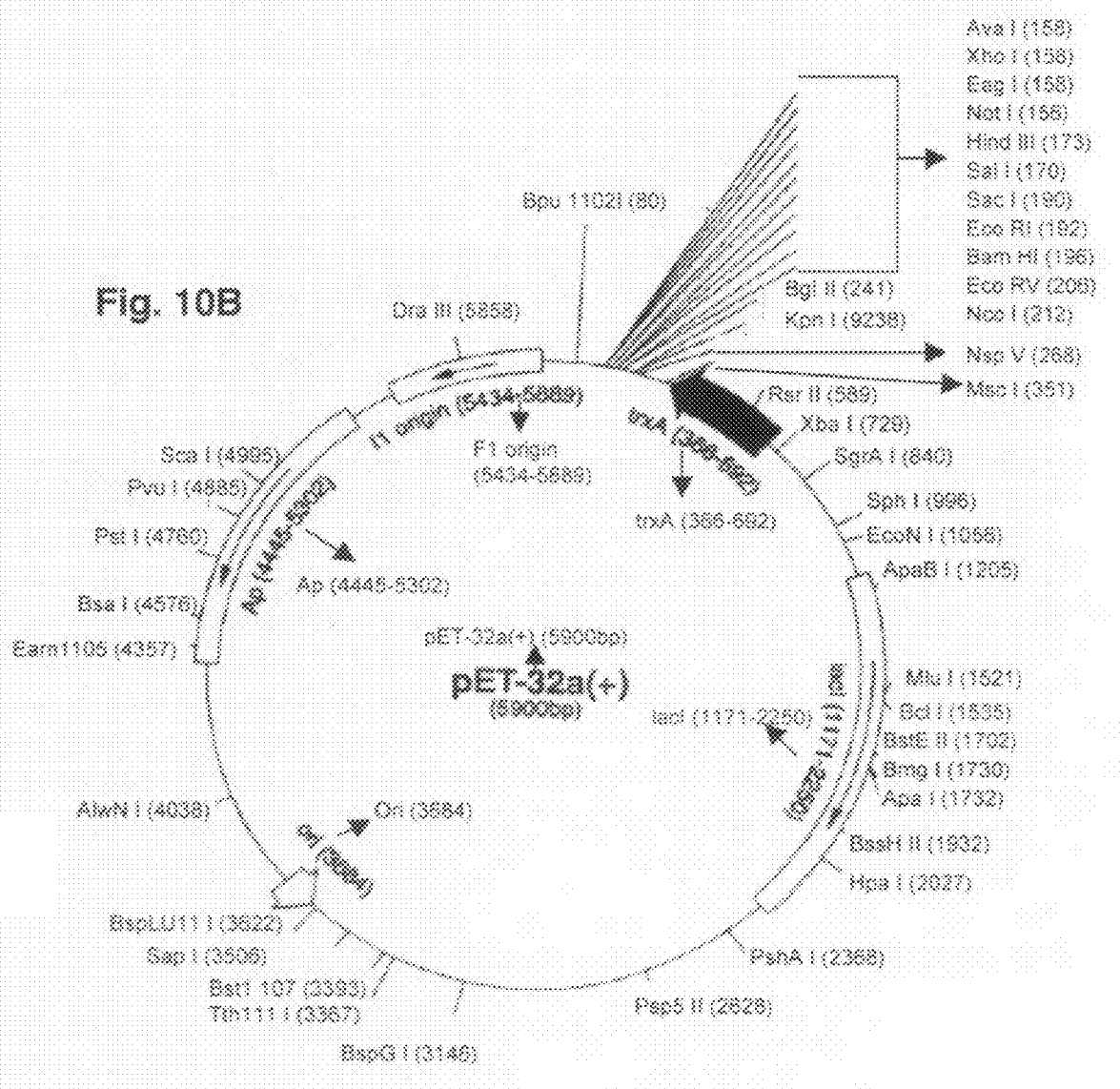

The *E. coli* vector containing the cDNA sequence for thioredoxin, upstream of hGastrin cDNA is shown in FIGS. 10A-10B. Additionally, FIGS. 10C-10F show the changes made in the hgastrin sequence to obtain efficient expression of progastrin peptide. The complete 80-amino acid sequence of the expressed hPG peptide from this vector is shown in FIG. 10G (SEQ ID NO: 3).

An etiological and prognostic role of gastrin gene/progastrin expression in relation to known genetic alterations in colon cancers (such as loss of APC and p53 functions and gain of c-myc, cyclin D1, β-catenin and K-ras oncogenic functions) is established to develop effective protocols for preventative and treatment purposes (Singh 2007). Differences in the expression of the gastrin gene in different types of hyperplastic/adenomatous growths and at different stages during adenoma-carcinoma sequence is being determined. Additionally, the levels of gastrin gene expression in tumors and serum progastrins are being correlated with the clinical status of the patients as a means of assessing prognostic value of measurements. Furthermore, in order to obtain reliable clinical data, the method of retrieval and storage of the specimens is examined to determine if the relative levels of gastrin gene expression (RNA and protein) are proportional to the serum progastrin levels. It is contemplated that the combined use of the progastrin containing fusion protein as a vaccine either alone or in combination with methods to down-regulate Annexin II, along with well established chemotherapeutic protocols will not only provide much higher treatment rates in patients with PG-expressing cancers but also improve the survival rates in these patients. Furthermore, since the gastrin gene and progastrin peptides are expressed in other cancers such as lung, breast, ovarian and pancreatic cancers besides colorectal cancers, the immunogenic compositions discussed herein may be used in treating the cancers that express the gastrin gene and are perhaps dependent on gastrin gene products (mainly progastrin) for their continued growth.

In summary, the immunogenic composition discussed herein may comprise progastrin or N-terminal or C-terminal fragments of progastrin fused with a non-human protein and formulated with an adjuvant and/or delivery systems. The progastrin may be a peptide comprising modified or unmodified amino acid sequences, recombinant progastrin or a fusion protein of human Progastrin and a non-human protein which includes but is not limited to thioredoxin, tetanus toxoid, diphtheria toxin, AraC, TrpR or Psts. The fusion protein disclosed herein may further have several variations which include but are not limited to a fusion protein of human Progastrin fused with non human proteins where multiple copies of Progastrin in tandem are fused with one or more nonhuman proteins, a fusion protein of human Progastrin fused with non human proteins where multiple copies of Progastrin in tandem are fused with one or more nonhuman proteins and has a tag at N terminal or C terminal such as hexa histidine, GST etc. or a progastrin fusion protein that is formulated with an adjuvant such as CFA, IFA, Rib, emulsion, MDPs, a polysaccharide, lipopolysaccharide DNA like CpGs sequences, liposomes, sustained delivery system such as PLGs, hydrogels like chitosan alginates, chitosan metal chelates etc. Furthermore, the immunogenic composition disclosed herein may be used to generate antibodies which can then be administered to the individual. It is contemplated herein that the instantly claimed immunogenic compositions are superior to the G17DT vaccine that is known in the art since the instantly claimed immunogenic compositions can be purified to a very high degree. The cancers that can be treated using the immunogenic composition disclosed herein include but are not limited to colon cancer, pancreatic cancer, lung cancer, ovarian cancer and breast cancer. Furthermore, the immunogenic compositions disclosed herein may be used in combination with Annexin II antibodies/siRNA and/or chemotherapy or in patients who have been previously treated with chemotherapy or radiation therapy.

The present invention is directed to a composition, comprising an agent targeting progastrin, where the agent comprises progastrin or a fragment thereof, an antibody directed against the progastrin or the fragment thereof or specific siRNA against progastrin, a pharmaceutically acceptable adjuvant, a delivery system or a combination thereof; or an agent targeting annexin II, where the agent comprises an antibody directed against annexin II, annexin II specific siRNA, annexin II specific antisense oligonucleotide, a pharmaceutically acceptable adjuvant, a delivery system or a combination thereof; or both of the agents. Since formulating such a composition is routine in the art, the agents may or may not be formulated in a pharmaceutically acceptable adjuvant or a delivery system.

The progastrin or the fragment thereof in such a composition may be a peptide, a recombinant protein or a fusion protein. Further, the peptide may comprise modified or unmodified amino acid residues of progastrin. The modified amino acids in the peptide may comprise alanine instead or arginine at position 36, 37, 73 and/or 74 and/or alanine instead of lysine at positions 53 and/or 54. Alternatively, the recombinant protein in such composition may be produced in E. coli, yeast, salmonella, BCG, vaccinia or other expression system.

Furthermore, the fusion protein in such composition may comprise multiple copies of progastrin in tandem fused with one or more non-human proteins or multiple copies of progastrin in tandem fused with one or more nonhuman proteins and tagged at N-terminal or C-terminal. The non-human protein in such fusion protein may include but is not limited to a protein from E. coli, yeast, streptococcus or other eukaryotes. The protein from other eukaryotes includes but is not limited to Tetanus Toxoid, Diphtheria toxin, AraC, TrpR or Psts. Additionally, the tag at the N or C-terminal is not limited to but may include hexa histidine, GST, cellulose binding protein, chitin binding protein, protein-A, protein-G or dihydrofolate reductase. Examples of the adjuvant include but is not limited to CFA, IFA, Rib, emulsion, MDPs, a polysaccharide or a lipopolysaccharide DNA. The lipopolysaccharide DNA may be a CpG sequence. Additionally, the delivery system includes but is not limited to a nanoparticle, liposome, PLG or hydrogel. Examples of the hydrogel include but is not limited to chitosan alginates or chitosan metal chelates. Furthermore, the composition may be a lyophilised powder that can be reconstituted, a suspension or an emulsion. Examples of routes of administering the composition discussed herein may include but is not limited to intramuscular, subcutaneous, intravenous, intranasal, oral or intrarectal routes. The amount of progastrin or a fragment thereof in such a composition may be 1 ug to 100 mg. The volume of the composition administered may be 100 ul to 2 ml.

The present invention is also directed to a method of inhibiting proliferation of a neoplastic cell, comprising: contacting the neoplastic cell with the composition discussed supra, where the composition comprises either an agent that targets progastrin or an agent that targets annexin II or both, such that the contact inhibits the growth-inducing activity of progastrin in the cell, thereby inhibiting the proliferation of the neoplastic cell. Generally, the composition may block binding of the progastrin to a receptor (Annexin II) on the cell, may block binding of a protein such as Annexin II that binds progastrin, may induce an immune response against progastrin or against receptors of progastrin, may downregulate expression of progastrin or annexin II at the nucleic acid level or protein level, may block internalization of progastrin in the cell or a combination thereof. Examples of the receptors of progastrin, include but is not limited to Annexin II, and those proteins that bind progastrin including, but not limited to proteins which have molecular mass ranging from 40-50 KDa. Additionally, the protein that binds progastrin may be an agonist or an antagonist of progastrin or an inhibitor of progastrin or progastrin binding molecule. The neoplastic cell contacted by the composition may be a cancer cell. Examples of cancer cell include but is not limited to colon cancer cell, breast cancer cell, lung cancer cell, pancreatic cancer cell or any other cancer cell that expresses gastrin gene or is dependent on gastrin gene products for growth.

The present invention is further directed to a method of treating a cancer in an individual, comprising: administering a pharmacologically effective amount of the composition discussed supra to said individual, wherein the composition comprises either an agent that targets progastrin or an agent that targets annexin II or both, such that the administration inhibits gastrin/progastrin-induced proliferation of cancer cells, thereby treating the cancer in the individual. This method may further comprise administering an anticancer drug to the individual. The anticancer drug may be administered prior to, concurrent with or sequentially to the administration. Generally, the anticancer agent may be a chemotherapeutic agent, an anti-angiogenic agent or an anti-epidermal growth factor agent. The chemotherapeutic agent, the anti-angiogenic agent or the anti-epidermal growth factor agent may be administered either alone or in combination. Examples of the chemotherapeutic agent may include but are not limited to 5 fluorouracil (5FU), Camptosar (CPT11), Eloxitan (Oxaliplatin), Lavamisol, Leucovorin or irinotecan. The anti-angiogenic agents may include but is not limited to Avastin and the anti-epidermal growth factor receptor family agents may include but is not limited to Erbitux.

Furthermore, the inhibition of proliferation may be due to blocking of binding of progastrin to a receptor, such as Annexin II, on the cell, blocking of binding of a protein that binds progastrin, eliciting an immune response against progastrin or receptors of progastrin, downregulating expression of progastrin or annexin II at the nucleic acid or protein level, blocking internalization of progastrin in the cell or a combination thereof. The individual benefiting from this method may be one who has high levels of progastrin, is in the primary stages of cancer, has full blown cancer, has tumors induced due to a growth-inducing effect of progastrin or has previously been subjected to chemotherapy or radiation therapy.

Examples of cancer may include but is not limited to colon cancer, breast cancer, lung cancer, pancreatic cancer or any other cancer that expresses gastrin gene or is dependent on gastrin gene products for growth.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "contacting" refers to any suitable method of bringing the composition or antibody described herein into contact with a neoplastic cell. In vitro or ex vivo may be achieved by exposing the above-mentioned cell to the composition in a suitable medium. For in vivo applications, any known method of administration is suitable as described herein As used herein, the term "pharmacologically effective amount" or "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "active immunization" is defined as the administration of a vaccine to stimulate the host immune system to develop immunity against a specific pathogen or toxin.

As used herein, "passive immunization" is defined as the administration of antibodies to a host to provide immunity against a specific pathogen or toxin.

As used herein, "CpG oligonucleotides" are defined by the presence of an unmethylated CG dinucleotide in a CpG motif.

As used herein, "adjuvant" is defined as a substance which when included in a vaccine formulation non-specifically enhances the immune response to an antigen.

The immunogenic composition disclosed herein and the antibody generated thereof may be administered either alone or in combination with another anticancer agent. Such an agent may be administered concurrently or sequentially with the immunogenic composition or antibody disclosed herein. The effect of co-administration with the immunogenic composition or antibody is to lower the dosage of the anticancer agent normally required that is known to have at least a minimal pharmacological or therapeutic effect against the disease that is being treated. Concomitantly, toxicity of the anticancer agent to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the anticancer agent may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunogenic composition or antibody described herein and the anticancer agent may be administered independently one or more times to achieve, maintain or improve upon a therapeutic effect. It is well within the skill of an artisan to determine dosage or whether a suitable dosage of either or both of the immunogenic composition or antibody and the anticancer agent comprises a single administered dose or multiple administered doses.

As is well known in the art, a specific dose level of such an immunogenic composition or antibody generated thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the immunologically effective amount of the immunogenic composition or the antibody generated thereof can be the amount that is required to achieve the desired result that is to enhance antibody response against progastrin and/or its receptors.

Administration of the immunogenic composition of the present invention and the antibody generated thereof to a patient or subject will follow general protocols for the administration of therapies used in treatment of cancer taking into account the toxicity, if any, of the components in the immunogenic composition, the antibody and/or, in embodiments of combination therapy. It is expected that the treatment cycles would be repeated as necessary. It also is contemplated that various standard therapies, as well as surgical intervention, may be applied in combination with the described therapy.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Role of Gastrin Gene Expression in Colorectal Carcinogenesis

The stage at which the gastrin gene is re-expressed/overexpressed during colorectal carcinogenesis is not known in humans. However, this information is important if gastrin gene expression and/or gastrin gene products (PG) are to be used as targets for treatment purposes. Hence, the present invention examined the level of expression of gastrin mRNA using real time quantitative RT-PCR in pinch biopsy of each polyp and surrounding normal mucosa of patients who had undergone colonoscopy. β-actin and/or 18SRNA was measured as an internal control. All values were expressed as a ratio of that in a normal mucosa sample that was arbitrarily chosen and assigned a value of one.

As shown in FIG. 2A-2D, ~75% of normal mucosal samples had negligible to low levels of gastrin gene expression. On the other hand, only 50% and 40% of hyperplastic (Hp) polyps and adenomas, respectively had low levels of gastrin gene expression. A large % of hyperplastic polyps and adenoma specimens (40-50%) and only 35% of normal mucosa were positive for low to moderate levels of gastrin gene expression. At least 20% of adenomas were positive for extremely high levels of gastrin gene expression that were >1000-fold higher than that in the arbitrarily chosen normal control. At least one adenoma sample from a patient was measured to express more than 100,000-fold excess of gastrin gene transcripts compared to the normal control. These results demonstrated for the first time that there was a great variation in the levels of gastrin gene expression in polyps. In spite of the small sample size, it became evident that on an average the relative levels of gastrin gene expression were higher in the hyperplastic polyps compared to that in the normal mucosa and that the levels were many fold higher in the adenomas compared to that in the hyperplastic polyps.

In order to control for possible inter-assay variations, the relative levels of gastrin gene expression in the polyps were compared to that in HCT-116 cells (wherein the relative level of gastrin gene expression in HCT-116 cells was arbitrarily assigned a value of 1.0). The gastrin gene expression levels, relative to that measured in HCT-116 cells, is presented in Table 1, in relation to the location of the polyp and the pathology of the polyp. The data once again demonstrated large variations, and the standard deviations ranged from 0.54 to 35,604. Therefore, the usual assumption of constant variance and normality will not apply herein. The relative level of expression of gastrin gene expression, on an average, was once again confirmed to be more than 1000-fold higher than that in HCT-116 cells in the adenomatous polyps (Table 1). The level of gastrin gene expression in the Hp polyps was also, on an average, 4 to 5-fold higher than that in HCT-116 cells. These results suggested that PG could potentially play an important role in the growth of a significant % of Hp polyps. In patients undergoing colonoscopy, at least one large polyp that was diagnosed as an adenocarcinoma (AdCA) (Table 1) was found to express relatively low levels of gastrin RNA. The gastrin RNA expression will be examined in many more AdCA samples in future.

It was interesting to note that the relative expression of gastrin RNA was many fold higher in polyps removed from either the proximal or the transverse (sigmoid) portions of the colon, while the levels appeared to be much lower in polyps from the descending colon and the rectum (Table 1). Equally surprising was the finding that ~60% of polyps were obtained from the ascending (proximal) colon and another 20% were obtained from the transverse section of the colon (Table 1). In animal studies, a predominance of pre-neoplastic lesions was reported in the proximal colon in mice over-expressing PG, which appears to resemble the prevalence of proximal polyps in humans as well (Singh et al, 2000b, 2000c, Cobb et al, 2004). It is thus possible that the etiology and risk factors dictating the prevalence of proximal colon carcinogenesis (in terms of Hp and Ad growths) may be similar in humans and in animal models over-expressing PG.

To confirm the rather unexpected finding that at least 50% of Hp polyps expressed significant levels of gastrin RNA (FIG. 2B, 2D), paraffin-embedded sections of representative polyps were examined immunocytochemically with specific anti-PG-Abs using previously described procedures (Cobb et al., 2004; Singh et al., 2000; Singh et al., 2000b; Singh et al., 2000c). A significant % of hyperplastic/dysplastic polyps stained variably for PG (FIG. 3A). Sections from at least one paraffin-embedded AdCA were also processed immunocytochemically with anti-PG-Ab, and was found to stain heavily for PG (FIG. 3A). Immunofluorescent staining confirmed a relative increase in the expression of progastrin associated with disease progression, wherein relative levels of PG were highest in adenocarcinomas followed by adenomas, with negligible expression in normal colons (FIG. 3B, Table II).

EXAMPLE 2

Growth Effects of Autocrine Progastrin (PG)

Since PG is the major form of gastrin expressed by primary colon cancers and colon cancer cell lines, the effect of specific antibodies on the growth of gastrin-dependent human colon cancer cells was examined. Specific anti-PG-AB at concentrations of 1:500 abolished the growth of gastrin-dependent cell lines (Colo-320, DLD-1, HCT-116) to basal, non-stimulated levels while anti-GG-Ab was much less effective and anti-G17-Ab was ineffective. Representative data from HCT-116 cells are presented in FIG. 5. Thus, it was confirmed that colorectal cancers do not express amidated gastrins.

EXAMPLE 3

Development of a rhPG Specific Vaccine

Since autocrine and endocrine PG might be playing an important role in colon carcinogenesis, the possibility of using an rhPG fusion protein as an immunogen for treatment purposes was examined. Briefly, the rhPG fusion protein (FP) was used as an immunogen in Balb/C, FVB/N and FABP-PG mice. The immunogen generated a strong response and very high titers of specific anti-hPG-Abs were measured within 4-8 weeks of vaccination. Data for Balb/c mice is shown in FIG. 6A. Mouse colon cancer (CA) cells are derived from Balb/C tumors and grow subcutaneously in Balb/C mice (Singh et al., 1986). The effect of high titers of anti-hPG-Abs in immunized mice was examined against the growth of CA cells in Balb/C mice (FIG. 6A). Mouse PG shares ~80% homology at the Cterminal end, and <65% homology at the N-terminal end, with hPG. CA tumor weights in mice treated with hPG-immunogen were reduced 15-30% compared to that in control mice. Additionally, in one mouse that demonstrated the highest Ab titer, tumors were not only the smallest, but also necrotic (FIG. 6A). Similarly, FVB/N mice, immunized against hPG-FP, were treated with AOM to examine if anti-PG-Abs can reduce the risk of colon carcinogenesis in these mice. The total number of tumors (FIG. 6B) and tumor burden/mouse (FIG. 6C) were significantly ($p<0.05$) reduced in mice immunized against hPG peptide compared to mice immunized with the adjuvant alone.

Aberrant crypt forci (ACFs) are pre-neoplastic markers of colon carcinogenesis and represent dysplastic growth of colonic crypts, which is the earliest stage of pre-cancerous changes in the colonic mucosa as described in detail previously (Singh et al, 2000b). In a transgenic mouse model (PS21, Fabp-PG), which overexpressed human progastrin peptide in the colonic crypts (Cobb et al 2004), it was demonstrated that the mice were at very high risk for developing ACF and adenomas and adenocarcinomas in response to a carcinogen, azoxymethane (Cobb et al 2004). These mice were immunized with either thioredoxin, or the progastrin peptide alone or the fusion protein (FP) which contained thioredoxin and progastrin.

Briefly, transgenic mice expressing human progastrin (PS21) and wild type mice were divided into 3 groups and immunized with (a) recombinant thioredoxin, (b) a recombinant fusion protein where human progastrin was fused with thioredoxin and recombinant progastrin, all proteins were expressed in *E. coli* and purified from cell extract. Each protein was emulsified using CFA/IFA (Sigma) as an adjuvant. The mice that received vaccine emulsified using CFA on day 1 followed by two subsequent immunization using IFA on day 21 and day 42. All injections were administered subcutaneously. Mice were bled and serum prepared to estimate the titers once a week for 3 weeks, 15 days after the final immunization. Mice were sacrificed after receiving AOM injection and the colons were excised and fixed. The ACFs were then counted.

FIG. 7A shows the number of aberrant crypt foci (ACF)/PS21 transgenic mice or wild type mouse and FIG. 7B shows the total number of aberrant crypt foci/mouse colon. The antibody tires in serum were determined by solid phase ELISA using limiting dilution method. Briefly, 96 wells PVC ELISA plates (Falcon) were coated with 3 different recombinant protein expressed in *E. coli* that were used to vaccinate mice i.e. recombinant thioredoxin, Thioredoxin-PG fusion protein and recombinant PG. Recombinant proteins were dissolved in carbonate buffer pH 9.0 and coated at a concentration of 50 µg/50 µl/well. The plates were incubated overnight at 4° C. Following day the plates were flipped and the well were blocked with 100 µl 2% non fat dry milk (NFDM) and plated were incubated at 37° C. for 3-4 hours. The plated were then washed 3 times with phosphate buffered saline containing 0.5% tween-20 (PBST). The coated plated were then loaded with 100 µl PBST and stored at −20° C. till further use. To determine tires the serum was diluted in PBST and 50 µl of diluted was loaded into the well and further diluted serially using double dilution. The plated were incubated at 4° C. overnight. The plates were then washed 4 times with PBST and 50 µl of rabbit anti-mouse IgG from Biorad (diluted 1:3000) was added to each well and incubated for 3 hrs at 37° C. the plates were then washed and incubated with orthophenlyamine-HCl (8 mg/10 ml) containing 100 µl of $H_2O_2$ at 37° C. for 10 min. The reaction was stopped by 50 µl of 5N $H_2SO_4$. The ELISA plated were them read in plate reader at 490 nm. The titer value was defined as the inverse of highest dilution at which the OD was at least twice higher than the control preimmune serum.

Figure 7D:
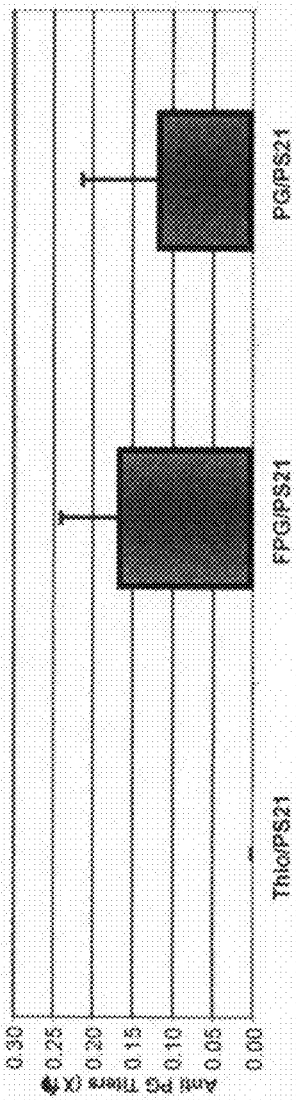
Figure 7E:
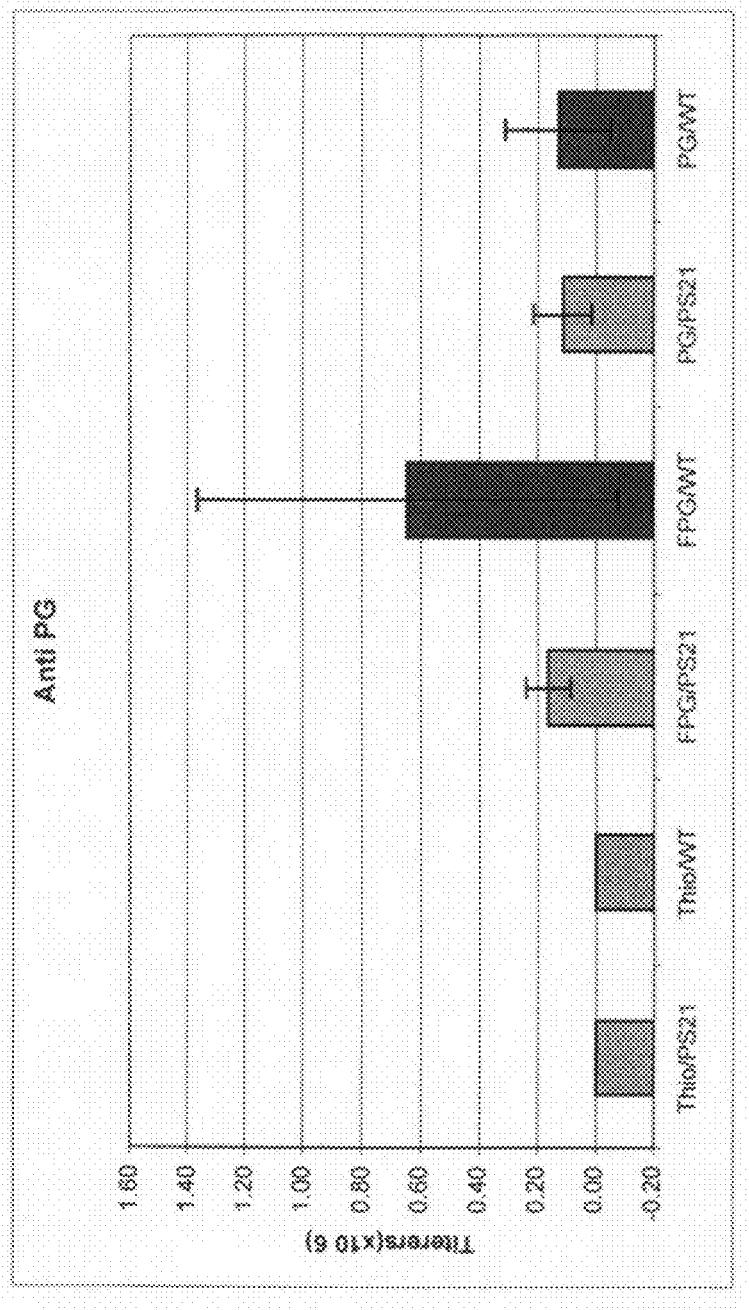

Mice that were immunized with the PG peptide alone demonstrated much lower levels of anti-PG-antibody titers, in both PS21 and WT mice, while mice immunized with the fusion protein demonstrated 2 fold to much higher titers of the anti-PG antibodies, especially in the WT mice (FIGS. 7C, 7D). The generation of PG antibodies (while 2 fold higher in PS21 mice injected with FP compared to PS21 mice injected with PG alone), was relatively attenuated in FP injected PS21 versus WT mice, which may reflect high levels of hPG since birth in PS21 mice, which is probably recognized as a self antigen. There is thus a good possibility that in mice/humans vaccinated against FP, the anti PG titres will be very high, since PG is not secreted at very high levels in wildtype animals. Mice immunized with thioredoxin demonstrated significant titers of anti-thioredoxin-antibodies in all the mouse groups (FIG. 7E). The development of ACF in response to AOM was significantly enhanced in PS21 mice immunized with either PG alone or with thioredoxin (FIG. 7A, 7B), as measured previously (Cobb et al, 2004). However, mice immunized with the fusion protein (FP) demonstrated a complete attenuation of the development of ACF in response to over-expressed PG, and the number of ACFs in the FP immunized PS21 mice reverted to control levels measured in wild type mice (FIG. 7A, 7B), providing strong evidence that colon carcinogenesis in response to progastrin can be effectively attenuated by immunizing with the fusion protein. Thus, the results presented herein indicated that the strategy of using progastrin peptides as immunogens would be extremely effective in neutralizing biological effects of PG.

EXAMPLE 4

Binding Affinity and Relative Binding Affinity (RBA) of Peptides for $^{125}$I rhPG Binding Sites Identification of PG Receptors as Annexin II The full-length recombinant human $PG_{1-80}$ (rhPG) was generated in an *E. coli* expression system and purified and confirmed as described previously (Singh et al, 2003). rhPG was radio labeled with $Na^{125}I$ (Amersham, Chicago, Ill.), and the intact $^{125}$I-rhPG purified by HPLC as described previously (Singh et al, 2003). For these experiments, AR42J cells were expanded in vitro in 175 mm flasks and grown to subconfluence in the growth medium containing 10% FCS. All binding assays were performed 36-48 h after seeding the cells in culture medium containing 10% FCS and 2% glutamine. Before the start of the binding assays, the cells in culture were washed with Hanks Balanced salt solution (HBSS) (GIBCO) containing 0.1% BSA and 25 mM HEPES (Sigma) and scraped with a rubber policeman into conical tissue culture polystyrene tubes. Cells were centrifuged at 500 g for 5 min and resuspended in HBSS at a concentration of $2 \times 10^6$ cells/ml. Aliquots (~1.0 ml) of suspended cells in polystyrene tubes were used in the binding assays. Binding assays were conducted as described previously (Singh et al 1995; Singh et al 2003). For purposes of determining binding affinity, a multipoint (7-12 points) saturation analysis was performed by using increasing concentrations (0.03-1.0 nM) of $^{125}$I-rhPG without (total binding) or with (non-specific binding) 1,000-fold excess of radio inert rhPG. The binding data was analyzed by a Scatchard plot as described previously (Singh et al, 1995). Binding assays were performed at 37° C. for 30-60 min at pH 6.5 (optimal for binding).

In order to define the RBA of various peptides for the PG binding sites on the cells, cells in suspension were incubated with 1.0 nM $^{125}$I-rhPG in the presence or absence of increasing concentrations (0.1 nM-10.0 µM) of either the homologous or heterologous peptide. Non-specific binding was determined in the presence of 1000× excess of the non-labeled homologous peptide. At the end of the incubation, the cells were pelleted and washed twice with 1 ml of fresh ice-cold HBSS plus 0.1% BSA. Cell pellets were counted for $^{125}$I in a gamma counter with ~70% efficiency for $^{125}$I. The RBA of gastrin-like peptides and/or competing peptides for binding the specific binding sites for rhPG were determined from a log-dose inhibition of specific binding of $^{125}$I-rhPG by various peptides as described previously (Singh et al, 1995). In a few experiments, $^{125}$I-Bolton Hunter-CCK-8 (Amersham Biosciences, Piscataway, N.J.) was used as the radiolabeled ligand and the RBA of gastrin like peptides for displacing the binding of $^{125}$I-BH-CCK8 to AR42J cells examined by our published methods (Singh et al, 1995).

It is by now well known that gastrin and progastrin peptides exert biological effects on target cells via novel binding sites that are separate from $CCK_2R$ (Rengifo-cam W. and Singh P, 2004)). Since $CCK_2R$ are expressed at high concentrations on AR42J cells (Singh et al, 1995), the relative binding affinity of gastrin-like peptides (PG, G17 and CCK) was examined for the high affinity CCK receptors and the high affinity PG binding receptors. As shown in FIG. 8, PG dose-dependently displaced the binding of radio-labeled rhPG (FIG. 8A, 8B), but was largely ineffective in displacing the binding of radio-labeled $^{125}$I-BH-CCK8 to $CCK_2R$ on the AR42J cells (FIG. 8C).

On the other hand, CCK and G17, both of which bind $CCK_2R$ with high affinity (Rengifo-Cam W and Singh P, 2004), demonstrated a negligible binding affinity for the PG binding sites (FIG. 8A, 8B), but completely displaced the binding of $^{125}$I BH-CCK8 (FIG. 8C). These results confirm that PG does not bind $CCK_2R$, but binds novel receptors with high affinity, which was recently confirmed to be annexin-II (Singh et al, 2007). Annexin-II has been shown to play an important role in mediating growth factor effects of PG on colon cancer cells (Singh et al, 2007), intestinal epithelial cells (FIG. 4D, 4E (panel i)) and pancreatic cancer cells (FIG. 4E (panel ii)) (Singh et al 2007, Rengifo-Cam et al 2007, Singh 2007). Annexin II demonstrated avid binding to progastrin in vitro and in vivo (FIG. 4B, 4C (panels i-iii)), demonstrated a strong co-localization with progastrin in situ (FIG. 4C (panels i-iii)) and was required for binding and internalization of the progastrin peptide (FIG. 4F).

EXAMPLE 5

Relative Expression of CCK2R in Hyperplastic and Adenomatous Polyps and in Adenocarcinoma Samples Using Real Time quantitative RT-PCR, the relative levels of $CCK_2$ receptors in polyp and tumor specimens were also measured. As can be seen in FIG. 9B, low to negligible levels of $CCK_2R$ were measured in the normal mucosa of patients from whom polyps were obtained at the time of colonoscopy. None of the hyperplastic polyps and adenomas expressed detectable levels of $CCK_2R$ (FIG. 9B). In the frozen adenocarcinoma samples, and in the majority of the surrounding normal colonic mucosal samples from these patients, no $CCK_2R$ RNA was measured (FIG. 9C). Only one normal mucosal sample (obtained from the tumor bank from the corresponding CRC patients) was positive for $CCK_2R$ RNA (FIG. 9B). The presence of low levels of $CCK_2R$ in the normal colonic mucosa, and almost complete absence of $CCK_2R$ expression in the colonic growths (including hyperplastic growths) suggests that $CCK_2R$ does not play a role in colon carcinogenesis. If anything, the results presented herein suggest that down-regulation of $CCK_2R$ may be required or acquired during the process of initiation and progression of the colorectal cancer disease.

EXAMPLE 6

Sequences of the Vectors and Nucleic Acid Encoding the Peptides and Amino Acid Sequences of the Peptides Discussed Herein The complete description of the *E. coli* vector that was used for expressing the fusion protein containing bacterial thioredoxin and human progastrin is presented in FIGS. 10A and 10B. The description of the vector is provided as text in FIG. 10B in some detail, and is self-explanatory. The hGastrin cDNA sequence is shown in SEQ ID NO: 1. The changes that were made in the hGastrin cDNA sequence for purpose of codon optimization (SEQ ID NO: 2) in order to obtain efficient expression of the PG peptide from the *E. coli* system used, is provided in FIGS. 10C-10F. Once again the information is self-explanatory. Finally the 80 amino acid sequence of the human PG peptide (SEQ ID NO:3) thus expressed and confirmed by mass spectrophotometery and by sequencing is presented in FIG. 10G. The symbol for each amino acid is shown.

The following references were cited herein:
Brown et al, Endocrinology 2003, 144: 201-211.
Cobb et al, Cancer 2004, 100: 6 1311-1323.
He and Marshall, Expert review of anticancer therapy 2006, 6(4): 487-492.
Olivo and Wargovich, In Vivo 1998, 12: 159-166.
Rengifo-Cam et al, Cancer Research 2007, 67 (15), 7266-74.
Rengifo-Cam and Singh, Curr Pharmaceutical Design 2004, 10: 2345-2358.
Rosenberg et al., Nat Med 2004, 10(9): 909-915.
Seva et al., Science 1994, 265: 410-412.
Siddheshwar et al, Gut 2001, 48: 47-52.
Singh et al, Cancer Res 1996, 56: 4111-4115.
Singh et al, Curr Opin Gastroentrol 2000a; 16:68-77.
Singh et al, J Biol Chem 1995, 270: 8429-8438.
Singh et al, Am J Physiol Gastrointest Liver Physiol 2003, 284: G328-G339.
Singh et al, Oncogene 2007, Vol. 26, No. 3, 425-440.
Singh and Cobb, Gastrin in the New Millennium 2004, 319-327.
Singh et al, Am J Physiol Gastrointest Liver Physiol 2000b, 278: G390-G399.
Singh et al, Gastroenterology 2000c, 119: 162-171.
Singh, Cancer Letters, 2007 252, 19-35
Takayama et al, N Engl J Med 1998, 339: 1277-1284.
Wu et al, Am J Physiol Gastrointest Liver Physiol 2003, 285: G1097-G1110.

What is claimed is:

1. A method of inhibiting proliferation of a colon, pancreatic or gastrointestinal cancer cell, comprising:

contacting the cell with a composition comprising an agent targeting annexin II, wherein said agent comprises an antibody directed against annexin II, and a pharmaceutically acceptable adjuvant, or a delivery system or both such that said contact inhibits the growth-inducing activity of progastrin in the cell, thereby inhibiting the proliferation of the colon, pancreatic or gastrointestinal cancer cell.

2. The method of claim 1, wherein said composition blocks binding of the progastrin to annexin II as a receptor on the cell.

3. The method of claim 2, wherein the receptor is annexin II.

4. A method of treating colon, pancreatic or gastrointestinal cancer in an individual, comprising:

administering pharmacologically effective amount of the composition comprising an antibody targeting annexin II, wherein said antibody is directed against annexin II, and a pharmaceutically acceptable adjuvant, or a delivery system or both to said individual, wherein said administration inhibits gastrin-induced proliferation of said cancer cells, thereby treating the colon, pancreatic or gastrointestinal cancer in the individual.

5. The method of claim 4, further comprising: administering an anticancer drug to the individual.

6. The method of claim 5, wherein the anticancer drug is administered prior to, concurrent with or sequentially with said composition comprising an antibody that targets annexin II, wherein said composition inhibits gastrin-induced proliferation of cancer cells.

7. The method of claim 5, wherein the anticancer agent is 5FU, Camptosar (CPT11), Eloxitan (Oxaliplatin), Lavamisol, Leucovorin, or irinotecan.

8. The method of claim 4, wherein said inhibition of proliferation is due to blocking of binding of progastrin to the receptor annexin II on the cell.

9. The method of claim 4, wherein the individual has detectable levels of progastrin, is in the primary stages of cancer, has tumors induced due to growth-inducing effect of progastrin or has previously been subjected to chemotherapy or radiation therapy.

* * * * *

SEQUENCE LISTING

```
<160> NUMBER OF SEQ ID NOS: 3

<210> SEQ ID NO 1
<211> LENGTH: 240
<212> TYPE: DNA
<213> ORGANISM: human
<220> FEATURE:
<223> OTHER INFORMATION: native coding sequence of gastrin gene
```

-continued

```
<400> SEQUENCE: 1
tcttggaagc cccgctccca gcagccagat gcacccttag gtacaggggc          50
caacagggac ctggagctac cctggctgga gcagcagggc ccagcctctc         100
atcatcgaag gcagctggga ccccagggtc ccccacacct cgtggcagac         150
ccgtccaaga agcagggacc atggctggag gaagaagaag aagcctatgg         200
atggatggac ttcggccgcc gcagtgctga ggatgagaac                    240

<210> SEQ ID NO 2
<211> LENGTH: 240
<212> TYPE: DNA
<213> ORGANISM: human
<220> FEATURE:
<223> OTHER INFORMATION: optimized coding sequence of gastrin gene

<400> SEQUENCE: 2
tcttggaaac cgcgcagtca gcaaccggat gcaccactgg gtacgggcgc          50
caaccgtgac ctggaattac cgtggcttga acagcaaggc ccagcctctc         100
atcatcgtcg ccagctgggc ccgcaaggtc caccctcactt agtggcggat         150 ccgtccaaaa agcagggacc atggctggaa gaggaagaag aggcctatgg         200
ttggatggat ttcggccgcc gtagtgcgga agatgagaac                    240

<210> SEQ ID NO 3
<211> LENGTH: 80
<212> TYPE: PRT
<213> ORGANISM: artificial sequence
<220> FEATURE:
<223> OTHER INFORMATION: sequence of progastrin peptide expressed by
      recombinant expression vector

<400> SEQUENCE: 3

Ser Trp Lys Pro Arg Ser Gln Gln Pro Asp Ala Pro Leu Gly Thr
                 5                  10                  15

Gly Ala Asn Arg Asp Leu Glu Leu Pro Trp Leu Glu Gln Gln Gly
             20                  25                  30

Pro Ala Ser His His Arg Arg Gln Leu Gly Pro Gln Gly Pro Pro
             35                  40                  45

His Leu Val Ala Asp Pro Ser Lys Lys Gln Gly Pro Trp Leu Glu
             50                  55                  60

Glu Glu Glu Glu Ala Tyr Gly Trp Met Asp Phe Gly Arg Arg Ser
             65                  70                  75

Ala Glu Asp Glu Asn
             80
```